(12) United States Patent
Eliad et al.

(10) Patent No.: US 11,642,103 B2
(45) Date of Patent: May 9, 2023

(54) METHODS AND SYSTEMS FOR MEDICAL IMAGING

(71) Applicant: General Electric Company, Schenectady, NY (US)

(72) Inventors: Shabtay Eliad, Zichron Yaakov (IL); Ross Christopher Stalter, Hartland, WI (US); Moshe Sela, Haifa (IL); Tanya Lynn Specht, Hempstead, NY (US); Craig Robert Loomis, Shorewood, WI (US); Milman Shmuel, Zichron Yaakov (IL); William Zang, Grafton, WI (US)

(73) Assignee: General Electric Company, Schenectady, NY (US)

( * ) Notice: Subject to any disclaimer, the term of this patent is extended or adjusted under 35 U.S.C. 154(b) by 349 days.

(21) Appl. No.: 16/241,732

(22) Filed: Jan. 7, 2019

(65) Prior Publication Data
US 2020/0214669 A1 Jul. 9, 2020

(51) Int. Cl.
*A61B 8/00* (2006.01)

(52) U.S. Cl.
CPC .......... *A61B 8/4427* (2013.01); *A61B 8/4444* (2013.01); *A61B 8/56* (2013.01); *A61B 8/4209* (2013.01); *A61B 8/4433* (2013.01); *A61B 8/467* (2013.01)

(58) Field of Classification Search
CPC ... A61B 8/4209; A61B 8/4427; A61B 8/4433; A61B 8/4444; A61B 8/467; A61B 8/56
See application file for complete search history.

(56) References Cited

U.S. PATENT DOCUMENTS

| | | | |
|---|---|---|---|
| 6,447,451 B1 | 9/2002 | Wing et al. | |
| 6,971,197 B1* | 12/2005 | Seiber | G09F 7/18 40/530 |
| 6,980,419 B2 | 12/2005 | Smith et al. | |
| 2014/0001315 A1* | 1/2014 | McNeal | H04Q 1/02 248/67.7 |
| 2015/0227127 A1* | 8/2015 | Miller | G16H 20/13 700/244 |
| 2016/0228091 A1* | 8/2016 | Chiang | A61B 8/0883 |

(Continued)

OTHER PUBLICATIONS

Sharkclean (Owner's guide, NV351, NV352; NV351.NV352.ES. 101207, sharkclean, EURO-PRO Operating LLC, Oct. 12, 2008) (Year: 2008).*

*Primary Examiner* — Yi-Shan Yang
*Assistant Examiner* — Alexei Bykhovski
(74) *Attorney, Agent, or Firm* — McCoy Russell LLP

(57) ABSTRACT

Various methods and systems are provided for a portable ultrasound imaging system. In one example, a portable ultrasound imaging system is disclosed, comprising a support stand with a sliding portion vertically slidable in relation to a stationary portion; a cradle configured to support an ultrasound imaging device and coupled to the sliding portion of the support stand; a tray, positioned below the cradle, coupled to the sliding portion of the support stand; and a case at least partially enclosing an electric power converter including an electric power cable, electrically coupled to the ultrasound imaging device, and positioned at a rear side of the support stand and coupled to the sliding portion of the support stand such that the sliding portion and the case move in unison during sliding movement of the sliding portion.

16 Claims, 16 Drawing Sheets

(56) References Cited

U.S. PATENT DOCUMENTS

| | | | | |
|---|---|---|---|---|
| 2016/0288151 A1* | 10/2016 | Schultz | ................ | F16M 11/105 |
| 2017/0027541 A1* | 2/2017 | Henderson | ........... | A61B 8/4405 |
| 2019/0223836 A1* | 7/2019 | Muramatsu | .............. | A61B 8/56 |
| 2019/0328229 A1* | 10/2019 | Sanchez | ................. | H04N 7/144 |
| 2019/0333426 A1* | 10/2019 | Boswell | ................... | G09F 9/33 |

* cited by examiner

METHODS AND SYSTEMS FOR MEDICAL IMAGING

FIELD

Embodiments of the subject matter disclosed herein relate to diagnostic medical imaging, and more particularly, to ultrasound imaging.

BACKGROUND

An ultrasound imaging system typically includes an ultrasound probe that is applied to a patient's body and a workstation or device that is operably coupled to the probe. The probe may be controlled by an operator of the system and is configured to transmit and receive ultrasound signals that are processed into an ultrasound image by the workstation or device. The system may be electrically powered by connecting the ultrasound imaging system to a power source, such as an electrical outlet. In one example, a cable conducts power from the outlet to an AC/DC converter coupled to the ultrasound imaging system.

BRIEF DESCRIPTION

One embodiment includes a portable ultrasound imaging system comprising a support stand with a sliding portion vertically slidable in relation to a stationary portion; a cradle configured to support an ultrasound imaging device and coupled to the sliding portion of the support stand; a tray, positioned below the cradle, coupled to the sliding portion of the support stand; and a case at least partially enclosing an electric power converter including an electric power cable, electrically coupled to the ultrasound imaging device, and positioned at a rear side of the support stand and coupled to the sliding portion of the support stand such that the sliding portion and the case move in unison during sliding movement of the sliding portion.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present invention will be better understood from reading the following description of non-limiting embodiments, with reference to the attached drawings, wherein below:

FIG. 9A shows the ultrasound imaging assembly of the first embodiment in a first position.

FIG. 9B shows the ultrasound imaging assembly of the first embodiment in a second position.

FIGS. 1-17 are shown approximately to scale. However, other relative dimensions may be used in other embodiments.

DETAILED DESCRIPTION

Figure 1:
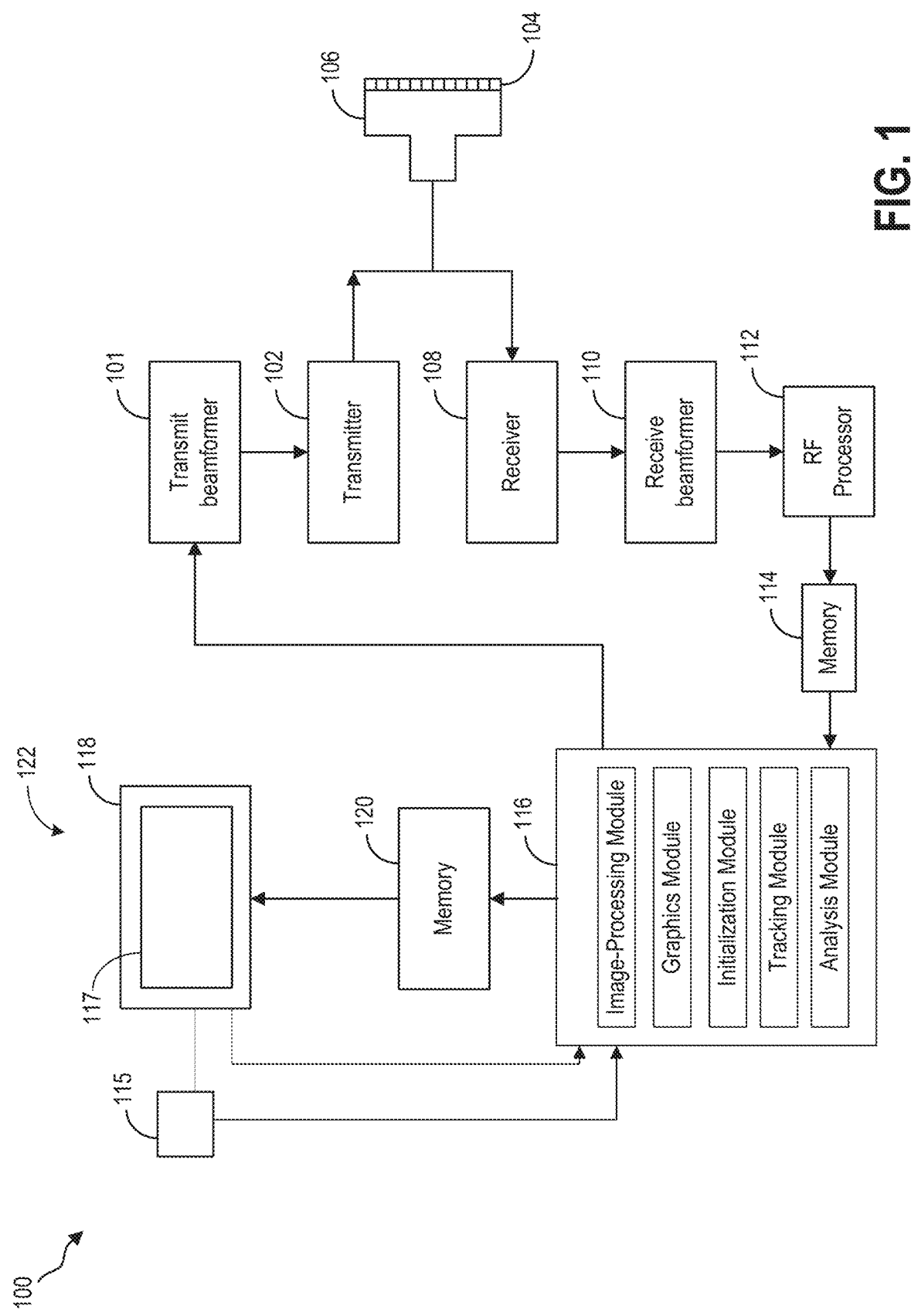
FIG. 1 shows an example ultrasound imaging system, according to an embodiment.

A portable ultrasound imaging system may be used as a device to enable medical imaging of patients with a capacity to be readily relocated to accommodate positioning of objects, personnel, and a patient in a given space. Components of the portable ultrasound imaging system, such as a graphical display and a tray, may be supported by a column providing a backbone to the system. It may be desirable to configure an overall height of the portable ultrasound imaging system to be adjustable, thereby enabling a height of each of the components to be modified according to an operator's preferences. However, depending on a number of components where height variation is desired, adjustment of each component individually may be time consuming and inefficient. Furthermore, the portable ultrasound imaging system may rely on a power pack including electrical cables coupling the system to an electrical outlet to deliver power to the system. The power pack may also include an electrical converter arranged along the cables between the outlet and the portable ultrasound imaging system. Depending on a length of a cable connecting the AC/DC converter to the portable ultrasound imaging system, when the portable ultrasound imaging system is raised or lowered, the AC/DC converter may alternatively be suspended above a ground surface or dragged along the ground surface, increasing a likelihood of contact between the converter and external objects, leading to degradation of the converter over time.

The inventors herein have recognized the issues described above. As one example, the issues may be addressed by a portable ultrasound imaging system configured with a support stand that has a mobile portion and a stationary portion. Components of the portable ultrasound imaging system may be directly coupled to the mobile portion and not the stationary portion. For example, components including a cradle supporting a graphical display, a tray, and a power pack may all be coupled to the mobile portion of the support stand so that vertical movement of the mobile portion is translated to similar movement of the components. Height adjustment of all the components coupled to the mobile portion of the support stand is thereby simultaneously actuated and conducted by adjusting a height of a single component, for example, by adjusting the tray height. Thus, height adjustment of the portable ultrasound imaging system with components directly coupled to the mobile portion of the support stand is faster and more efficient. Additionally, by positioning the power pack, including an electrical converter housed in a case coupled to the mobile portion of the support stand by a mounting bracket, at a rear side of the portable ultrasound imaging system, a weight of the AC/DC converter may offset weights of the cradle, graphical display, and tray, all biased towards a front side of the portable ultrasound imaging system. As a result, a weight distribution of the portable ultrasound imaging system is maintained balanced. Furthermore, the positioning of the power pack allows the power pack to remain at a fixed distance from the other components of the system, alleviating any strain imposed on the power pack due to stretching of power cables when the height of the system is raised and enables organized and secure storage of the power cables on the portable ultrasound imaging system.

Figure 9:
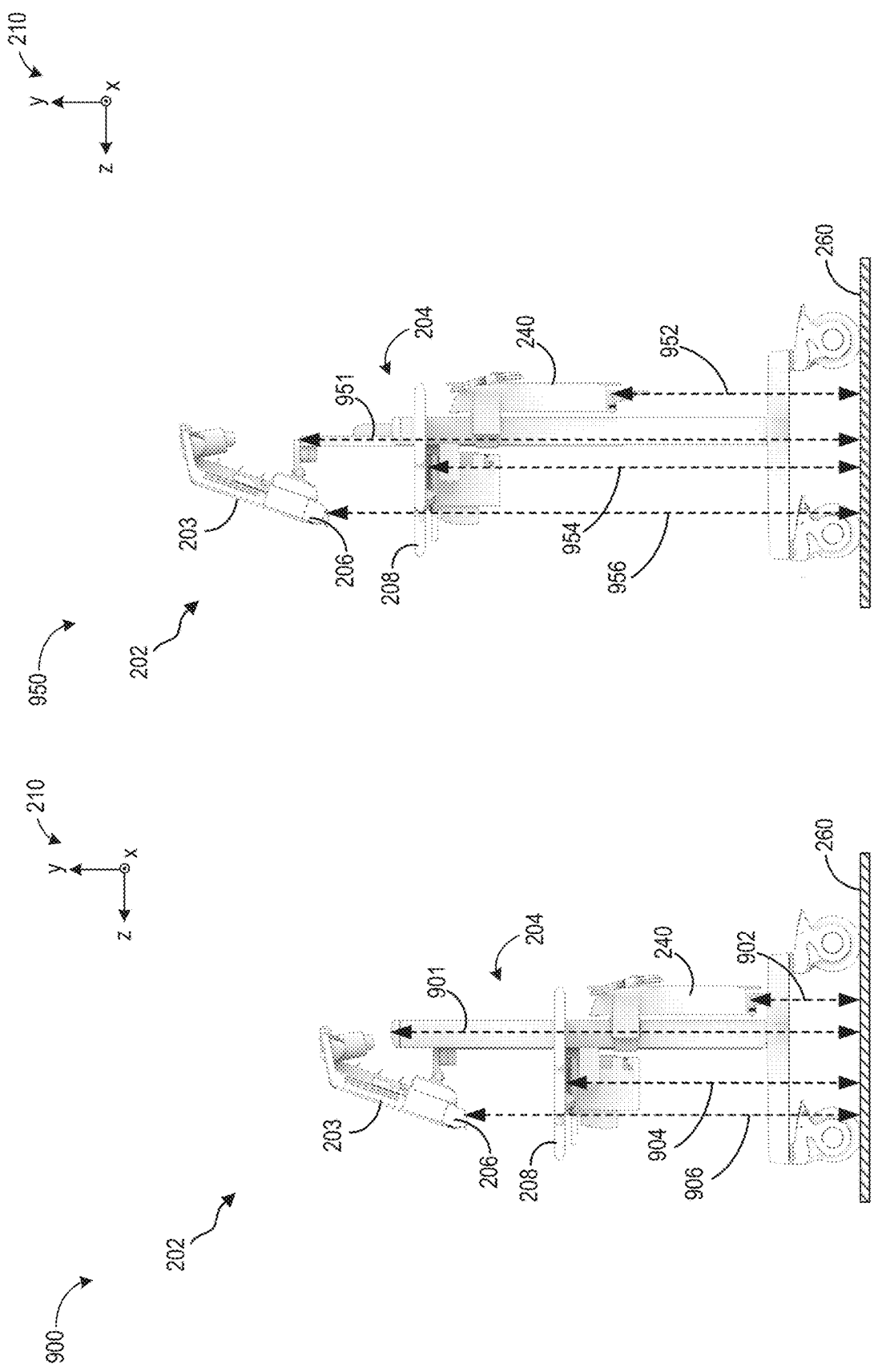
Figure 10:
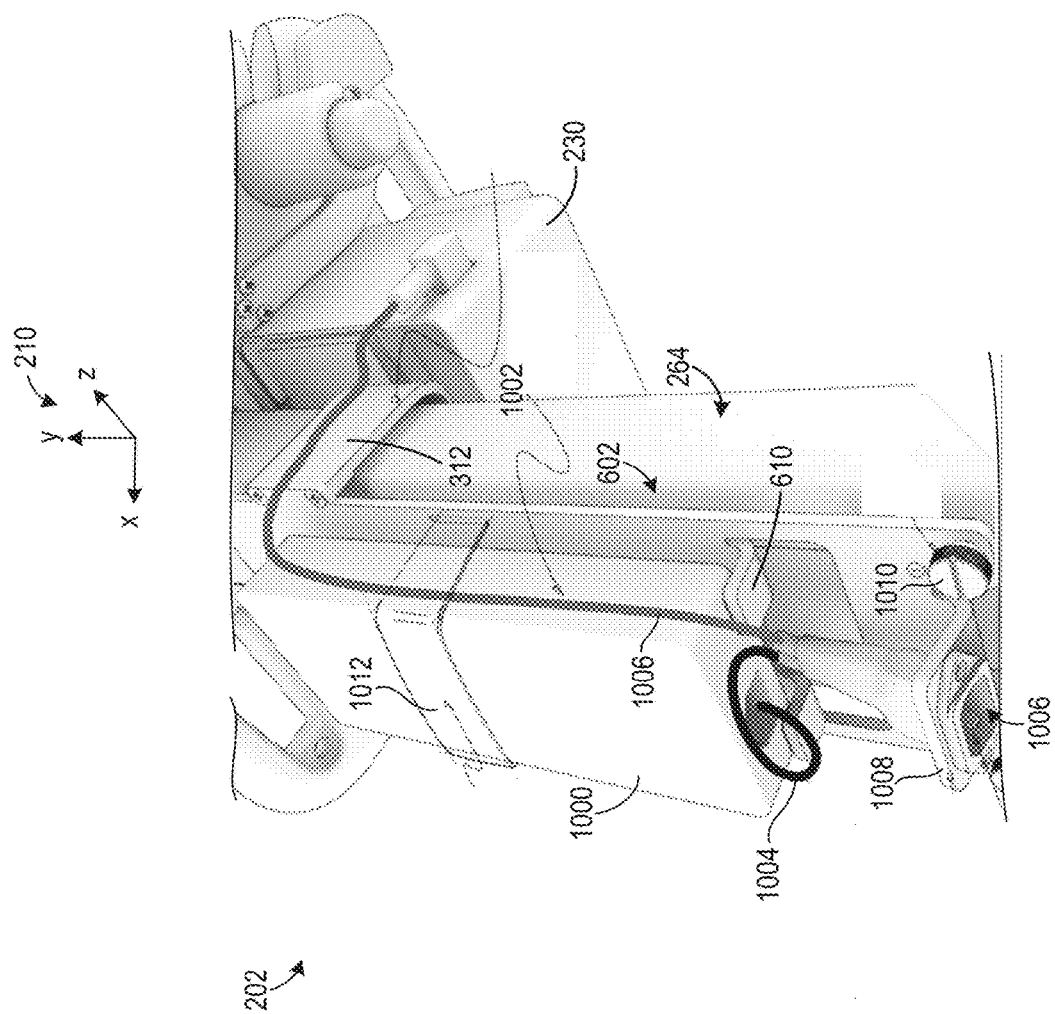
FIG. 10 shows a detailed view of a power pack supported by a mounting bracket in the ultrasound imaging system.
Figure 11A:
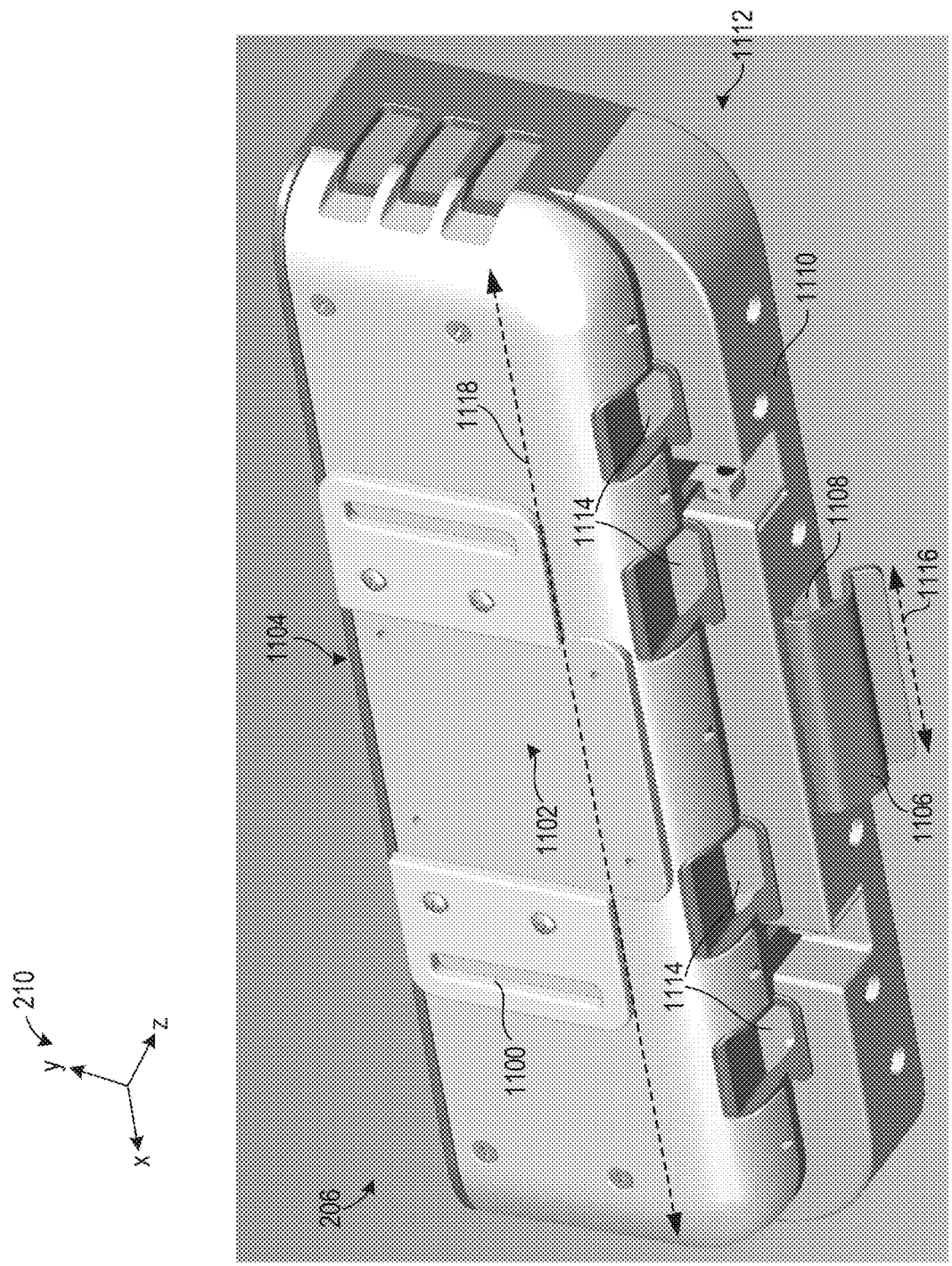
FIG. 11A shows a detailed rear view of a cradle included in the ultrasound imaging system.
Figure 16:
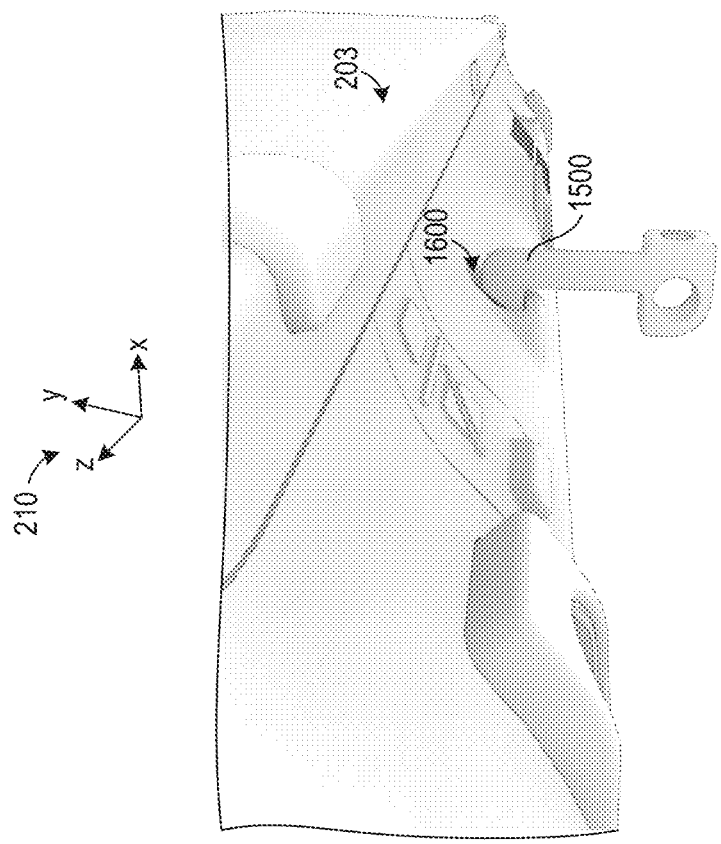
Figure 17:
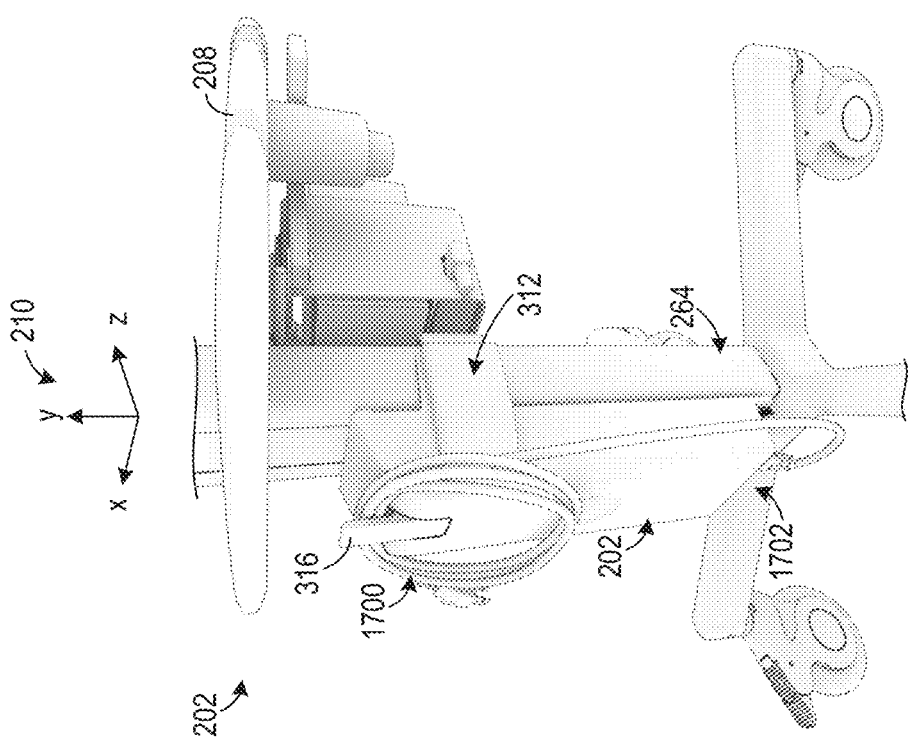
FIG. 17 shows a detailed view of a case slidingly coupled to a column in the ultrasound imaging system.

The following description relates to various embodiments of an ultrasound imaging system, such as the ultrasound imaging system shown in FIG. 1. The ultrasound imaging system is a portable ultrasound imaging system that that may be included within an ultrasound imaging assembly, such as the ultrasound imaging assembly shown by FIGS. 2-4, from a front view, a rear view, and a profile view, respectively. The ultrasound imaging assembly includes components such as a display, a tray, and an AC/DC converter. The components may be coupled to the ultrasound imaging assembly to slide up and down along a support column of the ultrasound imaging assembly as a single unit. Adjustment of the components between a first position and a second, higher position is illustrated in FIGS. 9A-9B. The AC/DC converter is shown in FIG. 5 from a rear perspective view of the ultrasound imaging assembly, depicted a positioning of the AC/DC converter along the support column as well as a cable management element of the AC/DC converter that allows one or more cables of the ultrasound imaging assembly to be stored. The support column of the ultrasound imaging assembly is shown with the AC/DC converter removed in FIG. 6 to illustrate a mounting assembly that couples the AC/DC converter to the support column. A wrapping of the mounting assembly around the support column is shown in a front view of the support column in FIG. 7. An orientation of the AC/DC converter when mounted to the support column is further depicted in a perspective view of the support column in FIG. 8. In this way, strain imposed on the cable and a likelihood of entanglement is reduced while maintaining a balanced positioning of the ultrasound imaging assembly components on the support stand. FIG. 10 shows a detailed view of a power pack supported by the mounting bracket in the ultrasound imaging system. Additionally, FIGS. 11A-12 show detailed views of a cradle and pivoting assembly included in the ultrasound imaging system. FIGS. 13-16 show different views of a release lever and associated mechanical components included in the cradle for releasing the portable imaging device from the cradle in the ultrasound imaging system. FIG. 17 shows a detailed view of a case slidingly coupled to a column in the ultrasound imaging system.

FIG. 1 illustrates a block diagram of a system 100 according to one embodiment. In the illustrated embodiment, the system 100 is an imaging system and, more specifically, an ultrasound imaging system. As shown, the system 100 includes multiple components. The components may be coupled to one another to form a single structure. In the examples described herein, system 100 is a unitary system that is capable of being moved (e.g., portably) from room to room. For example, the system 100 may include one or more components configured to couple the system 100 to a wheeled cart, similar to the system described below with reference to FIGS. 2-9B.

In the illustrated embodiment, the system 100 includes a transmit beamformer 101 and transmitter 102 that drives an array of elements 104 (e.g., piezoelectric crystals) within a diagnostic ultrasound probe 106 (or transducer) to emit pulsed ultrasonic signals into a body or volume (not shown) of a subject. The elements 104 and the probe 106 may have a variety of geometries. The ultrasonic signals are back-scattered from structures in the body, for example, blood vessels and surrounding tissue, to produce echoes that return to the elements 104. The echoes are received by a receiver 108. The received echoes are provided to a receive beamformer 110 that performs beamforming and outputs an RF signal. The RF signal is then provided to an RF processor 112 that processes the RF signal. Alternatively, the RF processor 112 may include a complex demodulator (not shown) that demodulates the RF signal to form IQ data pairs representative of the echo signals. The RF or IQ signal data may then be provided directly to a memory 114 for storage (for example, temporary storage).

The system 100 also includes a system controller 116 that includes a plurality of modules, which may be part of a single processing unit (e.g., processor) or distributed across multiple processing units. The system controller 116 is configured to control operation of the system 100. For example, the system controller 116 may include an image-processing module that receives image data (e.g., ultrasound signals in the form of RF signal data or IQ data pairs) and processes image data. For example, the image-processing module may process the ultrasound signals to generate slices or frames of ultrasound information (e.g., ultrasound images) for displaying to the operator. The image-processing module may be configured to perform one or more processing operations according to a plurality of selectable ultrasound modalities on the acquired ultrasound information. By way of example only, the ultrasound modalities may include color-flow, acoustic radiation force imaging (ARFI), B-mode, A-mode, M-mode, spectral Doppler, acoustic streaming, tissue Doppler module, C-scan, and elastography. The generated ultrasound images may be two-dimensional (2D) or three-dimensional (3D). When multiple two-dimensional (2D) images are obtained, the image-processing module may also be configured to stabilize or register the images.

Acquired ultrasound information may be processed in real-time during an imaging session (or scanning session) as the echo signals are received. Additionally or alternatively, the ultrasound information may be stored temporarily in the memory 114 during an imaging session and processed in less than real-time in a live or off-line operation. An image memory 120 is included for storing processed slices of acquired ultrasound information that are not scheduled to be displayed immediately. The image memory 120 may comprise any known data storage medium, for example, a permanent storage medium, removable storage medium, and the like. Additionally, the image memory 120 may be a non-transitory storage medium.

In operation, an ultrasound system may acquire data, for example, volumetric data sets by various techniques (for example, 3D scanning, real-time 3D imaging, volume scanning, 2D scanning with probes having positioning sensors, freehand scanning using a voxel correlation technique, scanning using 2D or matrix array probes, and the like). Ultrasound images of the system 100 may be generated from the acquired data (at the controller 116) and displayed to the operator or user on the display device 118.

The system controller 116 is operably connected to a user interface 122 that enables an operator to control at least some of the operations of the system 100. The user interface 122 may include hardware, firmware, software, or a combination thereof that enables an individual (e.g., an operator) to directly or indirectly control operation of the system 100 and the various components thereof. As shown, the user interface 122 includes a display device 118 having a display area 117. In the examples described herein, the display device 118 is a touchscreen display that enables the operator to adjust operating parameters of the system 100 by directly interacting with (e.g., touching) the display device 118. For example, the display device 118 may be configured such that when a user moves a finger/glove/stylus across the face of the display device 118, a cursor atop the ultrasound image on the display area 117 moves in a corresponding manner. The display device 118 may detect a presence of a touch from the operator on the display area 117 and may also identify a location of the touch in the display area 117. The touch may be applied by, for example, at least one of an individual's hand, glove, stylus, or the like. As such, the touch-sensitive display may also be characterized as an input device that is configured to receive inputs from the operator. The display device 118 also communicates information from the controller 116 to the operator by displaying the information to the operator. The display device 118 and/or the user interface 122 may also communicative audibly. The display device 118 is configured to present information to the operator during the imaging session. The information presented may include ultrasound images, graphical elements, user-selectable elements, and other information (e.g., administrative information, personal information of the patient, and the like). In some embodiments, the user interface 122 may be additionally configured to interface with (e.g., electronically couple to) one or more user interface input devices 115, such as a physical keyboard, mouse, and/or touchpad.

In addition to the image-processing module, the system controller 116 may also include a graphics module, an initialization module, a tracking module, and an analysis module. The image-processing module, the graphics module, the initialization module, the tracking module, and the analysis module may coordinate with one another to present information to the operator during and/or after the imaging session. For example, the image-processing module may be configured to display an acquired image on the display device 118, and the graphics module may be configured to display designated graphics along with the ultrasound image, such as graphical outlines, which represent lumens or vessel walls in the acquired image. The image-processing and/or graphics modules within the system controller 116, may also be configured to generate a 3D rendering or image (not shown) of the entire vascular structure.

In some embodiments, the system controller 116 may also house an image-recognition module (not shown), which accesses stored images/videos (e.g., an image library) from either or both of the memory 114 and the memory 120, before analyzing them. For example, knowing the parameters under which a protocol is being carried out (ultrasound type, scan plane, tissue being imaged, etc.) the image recognition module may compare a live image on the display area 117, to one stored in memory 120, in order to analyze the image and thereby improve the accuracy of placing and utilizing analytical tools. In an alternative embodiment, instead of utilizing an image recognition module and image library, the system controller may house instructions for analyzing acquired imaging data (e.g., ultrasound images/videos acquired with the probe) and automatically determining a desired placement of one or more analytical tools, such as a region of interest.

The screen of the display area 117 of the display device 118 is made up of a series of pixels which display the data acquired with the probe 106. The acquired data includes one or more imaging parameters calculated for each pixel, or group of pixels (for example, a group of pixels assigned the same parameter value), of the display, where the one or more calculated image parameters includes one or more of an intensity, velocity, color flow velocity, texture, graininess, contractility, deformation, and rate of deformation value. The series of pixels then make up the displayed image generated from the acquired ultrasound data.

Figure 2:
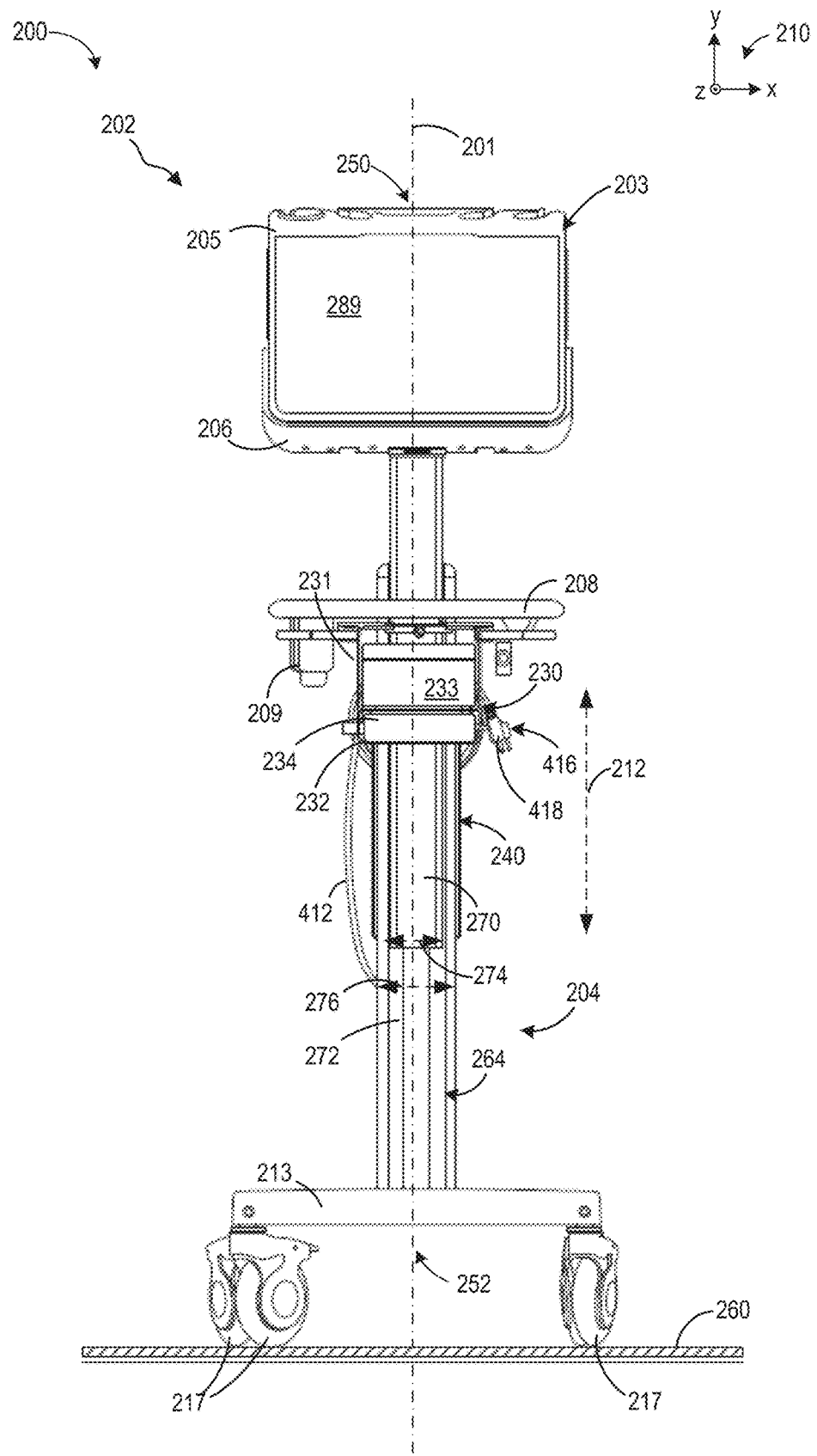
FIG. 2 shows a front view of a first embodiment of an ultrasound imaging assembly including a portable ultrasound system.
Figure 3:
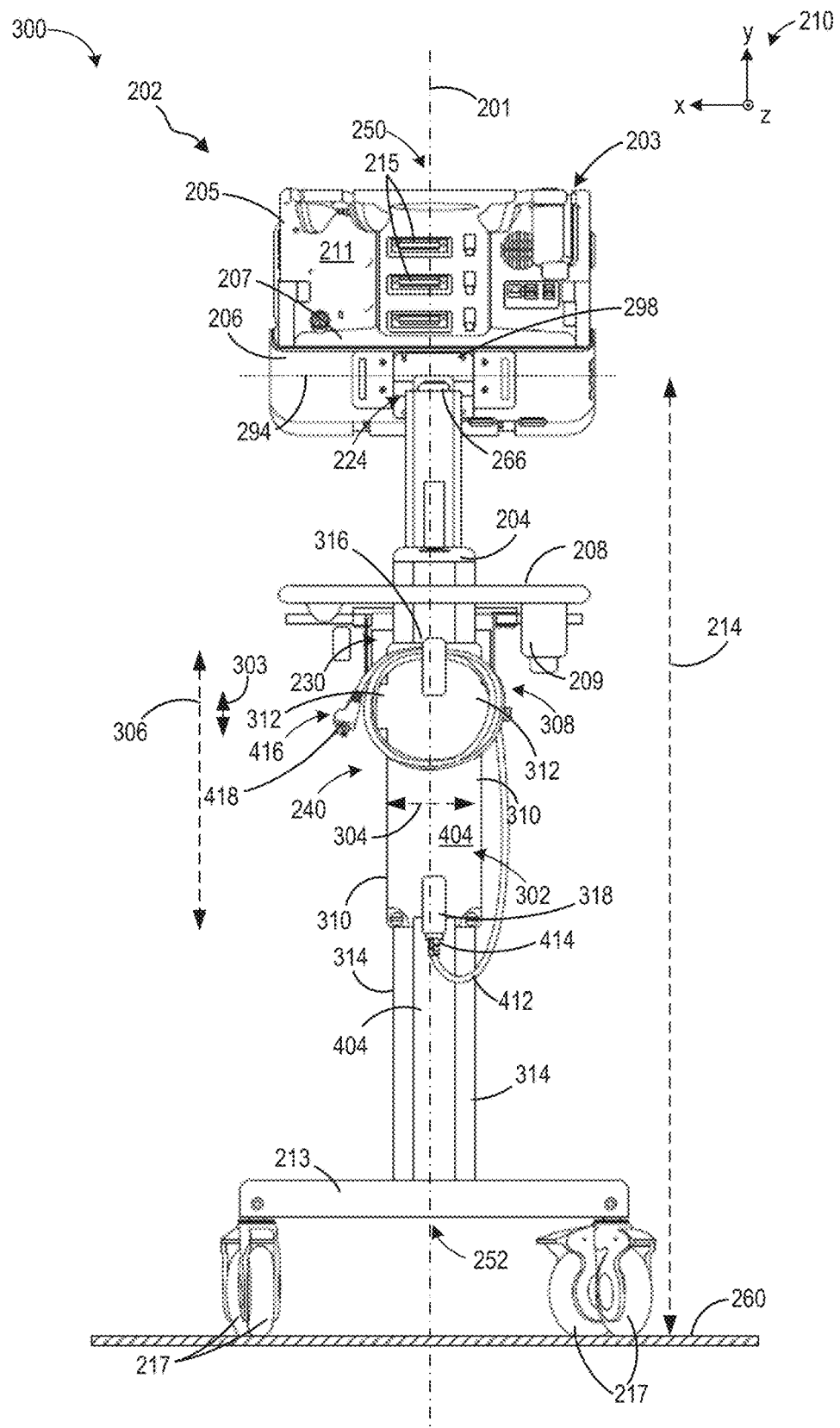
FIG. 3 shows a rear view of the ultrasound imaging assembly.
Figure 4:
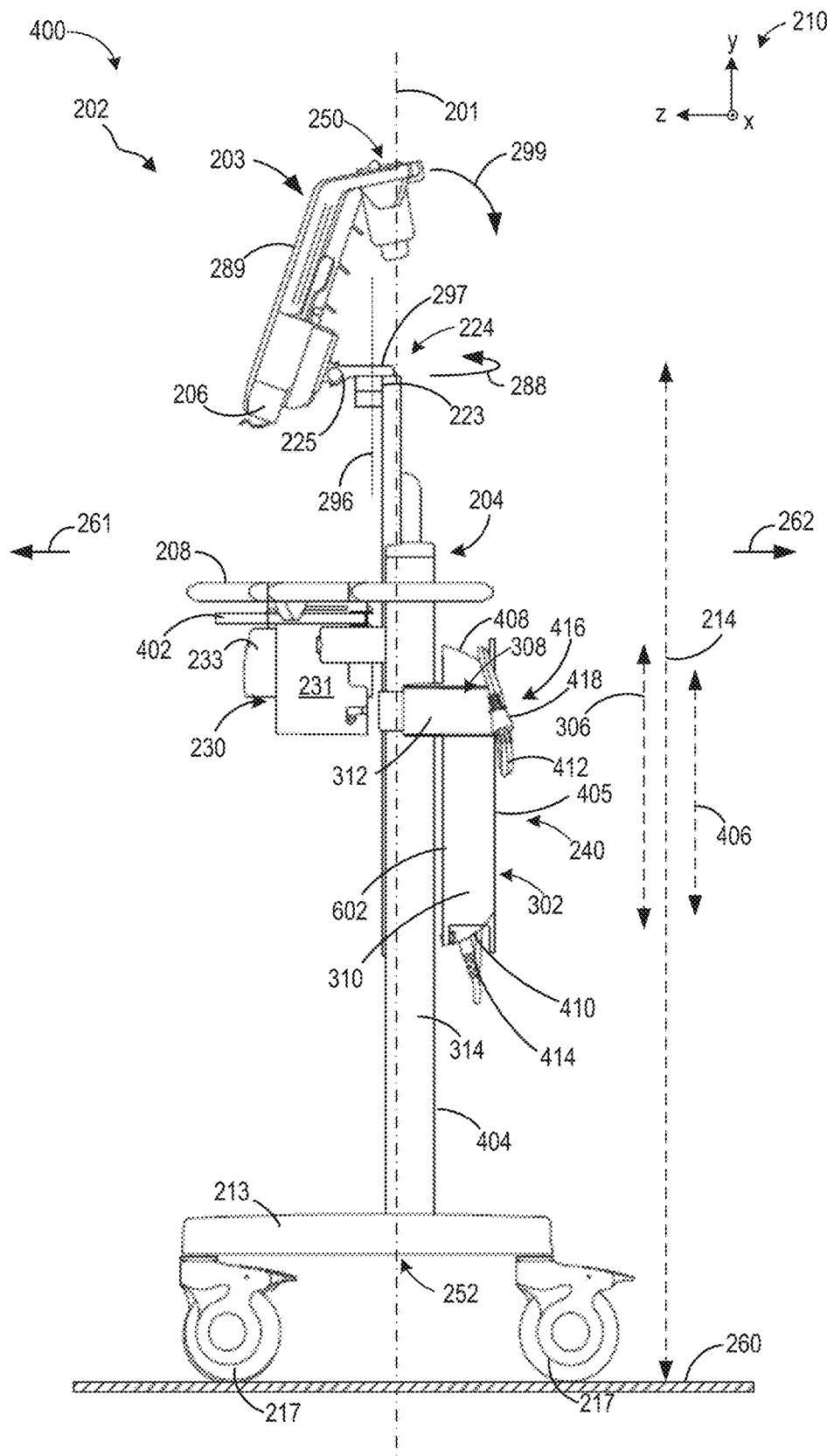
FIG. 4 shows a profile view of the ultrasound imaging assembly.
Figure 5:
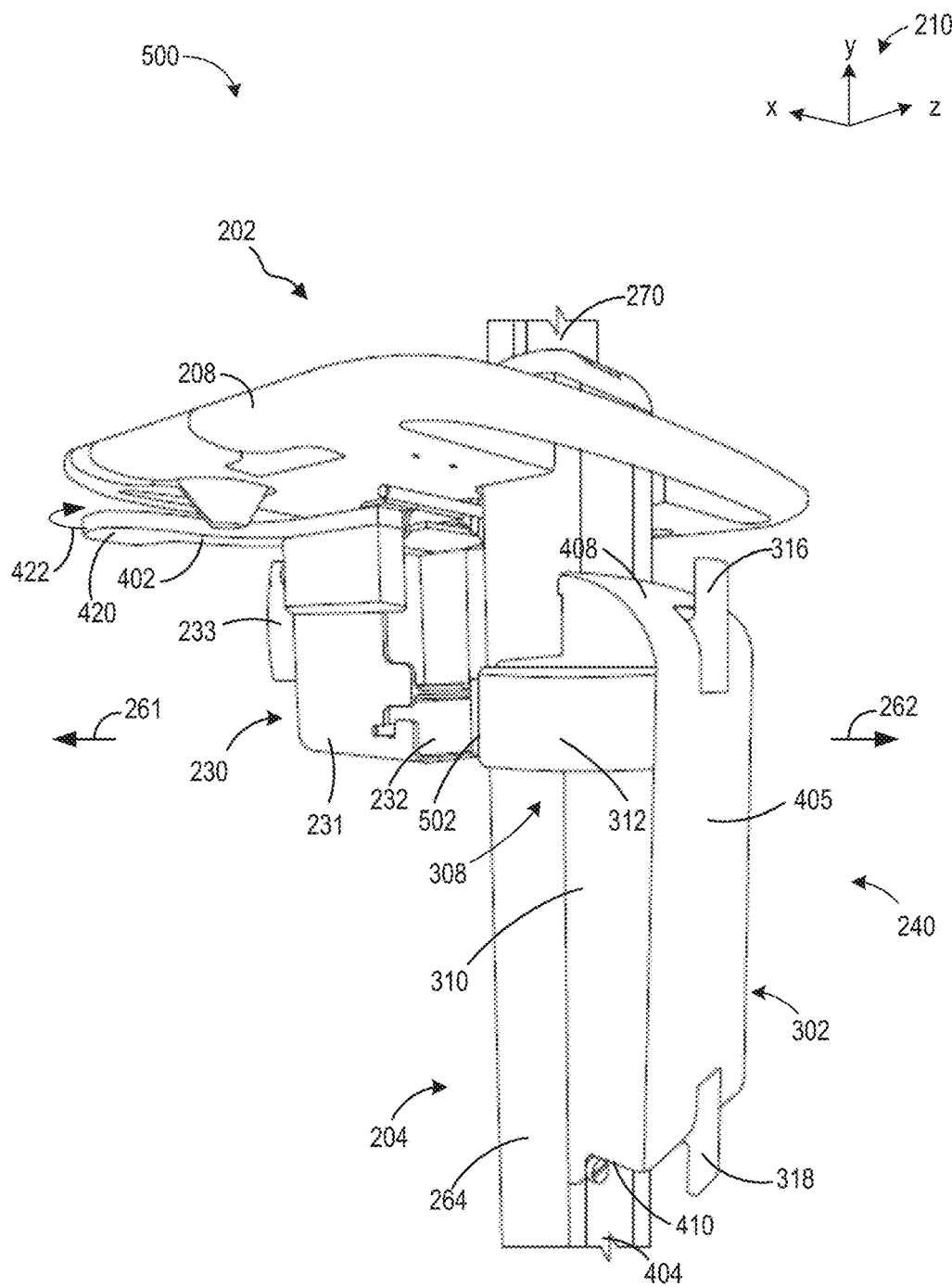
FIG. 5 shows a first perspective view of an AC/DC converter coupled to the ultrasound imaging assembly of FIGS. 2-4.

Turning now to FIGS. 2-4, a first embodiment of an ultrasound imaging system 202 is shown from a front view 200, a rear view 300, and a side view 400, respectively. In one example, the ultrasound imaging system 202 may be similar to the system 100 described above with reference to FIG. 1. The ultrasound imaging system 202 is a unitary system that may include at least some components of the system 100 of FIG. 1 and may be moved (e.g., portably) from room to room relative to the remainder of the ultrasound imaging system 202 which may stay in place and/or not be moved with the ultrasound imaging system 202. The ultrasound imaging system 202 may include several components similar to those described above with reference to system 100 (e.g., similar to display device 118, memory 120, system controller 116, probe 106, transmitter 102, receiver 108, etc.). A set of reference axes 210 are included in each of FIGS. 2-17 for comparison of the views shown, indicating a y-axis, an x-axis, and a z-axis. In some examples, as shown in FIGS. 2-17, the y-axis may be parallel with a vertical direction, the x-axis parallel with a horizontal direction, and the z-axis parallel with a transverse direction. Ultrasound imaging system 202 has an axis 201 that is parallel with the y-axis.

As shown in FIGS. 2-4, ultrasound imaging system 202 includes several components such as a portable imaging device 203, a support stand 204 aligned parallel with the axis 201, with tray 208, cradle 206, and an AC/DC converter, housed within a case 240, coupled to the support stand 204. The portable imaging device 203 may be an ultrasound imaging device such as device with a display such as a tablet with a touch screen. However, numerous suitable devices have been envisioned. The components of the ultrasound imaging system 202 may be coupled to the support stand 204 so that the ultrasound imaging system 202 may be readily relocated, e.g., moved to another area in a room or to another room, with the components attached to the support stand 204. The ultrasound imaging system 202 may also be configured to be height-adjustable, e.g., a vertical height, defined along the y-axis, may be varied by an operator to achieve a comfortable and ergonomic alignment of the components of the ultrasound imaging system 202 with the operator. For example, a taller operator may wish to raise the height of the portable imaging device 203 to be aligned with the operator's eyes. The taller operator may also desire raising of the tray 208 to provide more comfortable access to probes and accessories disposed on the tray 208.

As such, it may be desirable to adapt the ultrasound imaging system 202 with a configuration that allows the components of the ultrasound imaging system 202 to move in unison when the height is adjusted. As a result, the components do not demand individual, independent modification, which may be costly with regards to time and energy. By enabling the components to be adjusted simultaneously, the operational efficiency of the ultrasound imaging system 202 is increased. Furthermore, a balance of the ultrasound imaging system 202 components may be maintained by coupling the AC/DC converter to the ultrasound imaging system 202. In a conventional ultrasound system, the AC/DC converter may be connected at a first end to the ultrasound system by a first cable, and connected at a second end to a power outlet by a second cable. When the ultrasound system is moved from one location to another, strain may be imposed on connection points between the first cable and the AC/DC converter and between the first cable and other components of the ultrasound system to which the first cable may be coupled to, such as the portable imaging device 203. The second cable may be unplugged from the power outlet during relocation of the ultrasound system and drag on the floor or become tangled. In addition, raising of a height of the ultrasound system may result in the AC/DC converter being lifted off the floor, suspended by the first cable. A weight of the AC/DC converter may cause the ultrasound system to become unbalanced.

Coupling the AC/DC converter to the support stand 204 of the ultrasound imaging system 202, as shown in FIGS. 2-8 and described in detail further below, may provide advantages with regards to balanced weight distribution of the ultrasound imaging assembly components, reduced strain on cable connections between the AC/DC converter and other components, and efficient cable management to reduce entanglement of the ultrasound imaging assembly power cables and degradation of the cables and cable connection points. The AC/DC converter may be similarly connected to the support stand 204 as the tray 208 and the portable imaging device 203 so that as the height of the support stand 204 is adjusted, the AC/DC converter also moves vertically in unison with the tray 208 and the portable imaging device 203. The AC/DC converter is thereby maintained at a fixed distance from the other components coupled to the support stand 204 and configured to move vertically with the support stand 204. A positioning of the AC/DC converter at a rear side of the support stand 204 may assist in counterbalancing weights of the tray 208, the cradle 206, and the portable imaging device 203, all biased towards a front side of the support stand 204, and also position the AC/DC converter and cables coupled to the AC/DC converter in a region of the ultrasound imaging assembly that does not impede the operator's access to the tray 208 and the portable imaging device 203 during operation. In this way, height modification of the components of the ultrasound imaging assembly may be simplified to a single motion, thereby reducing an amount of time spent on adjusting each component of the ultrasound imaging system 202 to achieve comfortable positioning.

Variation of a height of the ultrasound imaging system 202 is illustrated in FIGS. 9A and 9B. In FIG. 9A, the ultrasound imaging system 202 is shown in a first position 900. The support stand 204 has a first height 901, relative to a ground surface 260. Components coupled to the support stand 204 include the case 240 housing the AC/DC converter, the cradle 206 supporting the portable imaging device 203, and the tray 208. The case 240 has a second height 902, measured as a distance between a bottom end of the case 240 and a ground surface 260. Similarly, the tray 208 has a third height 904, and the portable imaging device 203 has a fourth height 906, measured as a distance from the cradle 206 to the ground surface 260. The portable imaging device 203 may be a portable tablet with a display screen.

In FIG. 9B, the ultrasound imaging system 202 is raised to a second position 950 that is higher, relative to the y-axis, than the first position 900. In the second position 950, the support stand 204 has a fifth height 951 that is higher than the first height 901 of the support stand 204. A sixth height 952 of the case 240 is higher than the second height 902, a seventh height 954 of the tray 208 is higher than the third height 904 and an eighth height 956 of the cradle 206 is higher than the fourth height 906. The differences in heights between the first position 900 and the second position 950 of the tray 208, cradle 206, and case 240 are similar due to a unified shift upwards of the components to the second position 950 compelled by increasing the height of the support stand 204.

Turning now to FIGS. 2-4, the tray 208 is shown coupled to the support stand 204 between a first end 250 and a second end 252, with the cradle 206 positioned at the first, upper end 250. In some examples, one or more storage bins may be coupled to the support stand 204 to store accessory items. A plurality of casters 217 of the support stand 204 may be positioned at a second, lower end 252 of the ultrasound imaging system 202. Casters 217 are configured to support the support stand 204 against the ground surface 260 and to enable the support stand 204 to more easily move across the ground surface 260 (e.g., roll along the ground surface 260). In some examples, one or more of the casters 217 may be configured with a locking mechanism (e.g., a brake) configured to selectably lock the casters 217 and maintain a position of the support stand 204 relative to the ground surface 260 (e.g., reduce a likelihood of the casters 217 from rolling or otherwise moving relative to the ground surface 260).

The tray 208 may include one or more elements configured to enable the tray 208 to couple to the support stand 204. In some examples, tray 208 may include one or more grooves, tabs, etc., configured to engage with counterpart grooves, tabs, etc., of the support stand 204 in order to couple the tray 208 to the support stand 204. For example, tray 208 may include one or more tabs configured to engage with counterpart grooves of the support stand 204. In other examples, the tray 208 may be coupled to the support stand 204 via one or more fasteners (e.g., bolts). In some examples, the tray 208 may be slidable to a plurality of different positions along the support stand 204 (e.g., in a direction of the axis 201) and may be maintained in any of the plurality of positions via the fasteners, tabs and grooves, etc. Although tray 208 is shown by FIGS. 2-9B, in some examples the ultrasound imaging system 202 may not include the tray 208.

Furthermore, the tray 208 may include a plurality of openings and/or slots that may be shaped and/or positioned to accommodate various objects and accessories. For example, the tray 208 may include one or more openings adapted as handles to allow an operator to grasp the one or more handles and pull up or push down on the one or more handles to adjust a height of the tray 208, relative to the y-axis. As another example, tray 208 may have a probe holder 209, as shown in FIGS. 2-3, to accommodate a probe coupled to the ultrasound imaging system 202 and maintain a position of the probe within the tray 208. In other examples, the tray 208 may also be configured with a slot to allow passage of cables through the tray 208 and one or more openings to maintain positions of additional ultrasound imaging transducers or probes. In addition, the tray 208 may be adapted with a lever 402, as shown in FIGS. 4 and 5 and described further below, that enables or inhibits a movement of the support stand 204 to adjust a position of the tray 208 relative to an operator.

The tray 208, as well as the portable imaging device 203, the AC/DC converter housed within the case 240, and a printer assembly 230, may be coupled to the support stand 204 so that the said components may move in unison along the y-axis. The support stand 204 may be an elongate structure, aligned with the axis 201 and extending between the portable imaging device 203 and a base 213 to which the casters 217 are coupled. The support stand comprises two portions: a stationary column 264 that does not move along the y-axis, and a mobile sliding arm 270, as shown in FIG. 2. As such, the components coupled to the support stand 204, e.g., the tray 208, the case 240, etc., may be attached to the sliding arm 270 of the support stand 204 but not the column 264.

The sliding arm 270 is configured to slide vertically (e.g., along the y-axis), within a front channel 272 of the column 264, as illustrated in FIG. 2. The sliding arm 270 has a width 274, defined along the x-axis, the width 274 of the sliding arm 270 narrower than a width 276 of the column 264 and similar to a width of the front channel 272. The front channel 272 may be a track that constrains movement of the sliding arm 270, relative to the column 264, within the front channel 272 so that the sliding arm 270 may move up or down, as indicated by arrow 212 but not laterally, e.g., along the x-axis, or tilt, e.g., pivot at a radial angle relative to the axis 201.

As a result, the sliding arm 270 is adjustable between a fully retracted position, defined by a maximum distance that the sliding arm 270 may slide downwards along the axis 201 and retract into the column 264, and a fully extended position, defined by a maximum distance that the sliding arm 270 may slide upwards along the axis 201 and extend away from the column 264. The sliding arm 270 may be continuously adjustable between the fully retracted and fully extended positions. The fully retracted position may represent a shortest height of the ultrasound imaging system 202 and the fully extended position may represent a tallest height of the ultrasound imaging system 202.

As such, the support stand 204 is adjustable to a plurality of different heights via movement of the sliding arm 270 within the front channel 272. The tray 208 may be secured to the sliding arm 270 by any of the mechanisms described above, the portable imaging system coupled to a top end 266 of the sliding arm 270 via a pivot assembly 224, as shown in FIG. 3, and the AC/DC converter connected to the sliding arm 270 by a mounting assembly described further below. Each of the above components is coupled to the sliding arm 270 and not the column 264 of the support stand 204 so that movement of the sliding arm 270 is not impeded. Thus a height of the components, and of the support stand 204, may be simultaneously adjusted.

For example, the sliding arm 270 may slide along the axis 201, up or down as indicated by arrow 212 while the column 264 remains stationary. The support stand 204 may include one or more locking mechanisms (e.g., locking pins, levers, etc.) configured to maintain the sliding arm 270 at a plurality of different heights, and the support stand 204 may be adjusted to (and/or locked at) any of the plurality of different heights by the operator of the ultrasound imaging system 202. By adjusting the height of the support stand 204, the operator may adjust the positions of the tray 208, the AC/DC converter, the portable imaging device 203, as well as the pivot assembly 224, as shown in FIGS. 3 and 4, relative to the ground surface 260.

For example, increasing the height of the support stand 204 may increase a length 214, as shown in FIG. 3, between the pivot assembly 224 and the ground surface 260, and decreasing the height of the support stand 204 may decrease the length 214 between the pivot assembly 224 and the ground surface 260 (e.g., the length 214 in the direction of axis 201 and indicated in FIGS. 3-4). By increasing or decreasing the length 214 between the pivot assembly 224 and the ground surface 260 via adjusting the height of the support stand 204 as described above, a height of the portable imaging device 203 relative to the ground surface 260 (e.g., the length 214) may be adjusted during conditions in which the portable imaging device 203 is coupled to the support stand 204.

The cradle 206 of the ultrasound imaging system 202 is coupled to the support stand 204 via the pivot assembly 224. Pivot assembly 224 includes a plurality of pivots configured to enable the cradle 206 to pivot relative to the support stand 204. For example, as shown by FIG. 4, the pivot assembly 224 includes a first pivot 223 and a second pivot 225, with the first pivot 223 enabling the cradle 206 to pivot around axis 296, and with the second pivot 225 enabling the cradle 206 to pivot around axis 294 (as shown in FIG. 3). Axis 296 is parallel with axis 201 and the z-axis of reference axes 210, and axis 294 is perpendicular to axis 201 (e.g., axis 296 and axis 294 are perpendicular relative to each other).

Specifically, as depicted in FIG. 4, the pivot assembly 224 includes an arm 297 extending between the first pivot 223 and the second pivot 225 and coupled to each of the first pivot 223 and the second pivot 225, with the first pivot 223 coupling the arm 297 to the support stand 204 and with the second pivot 225 coupling the arm 297 to a mounting bracket 298, the mounting bracket 298 shown in FIG. 3. The mounting bracket 298 is pivotable relative to the arm 297 via the second pivot 225, and the arm 297 is pivotable relative to the support stand 204 via the first pivot 223. The first pivot 223 enables the cradle 206 to pivot around axis 296 and does not enable the cradle 206 to pivot in other directions via the first pivot 223. The second pivot 225 enables the cradle 206 to pivot around axis 294 and does not enable the cradle 206 to pivot in other directions via the second pivot 225. However, in other examples, one or both of the first pivot 223 and second pivot 225 may be configured differently (e.g., as ball joints) in order to enable pivoting of the cradle with more than one degree of freedom per pivot.

As shown in FIG. 3, mounting bracket 298 is fixedly coupled to cradle 206, such that the cradle 206 does not pivot relative to the mounting bracket 298 (or vice versa). In one example, the mounting bracket 298 may be coupled to the cradle 206 via one or more fasteners (e.g., bolts). By fixedly coupling the mounting bracket 298 with the cradle 206, and by enabling the mounting bracket 298 to pivot around axis 294 via the second pivot 225, an angle of the portable imaging device 203 may be adjusted relative to the support stand 204 (and relative to the ground surface 260). For example, during conditions in which the portable imaging device 203 is coupled to the support stand 204 (e.g., by seating the portable imaging device 203 in the cradle 206 and locking the portable imaging device 203 to the cradle 206, as described below), the portable imaging device 203 may be pivoted toward and/or away from the support stand 204 and ground surface 260 via the mounting bracket 298 coupled to the second pivot 225 (e.g., as indicated by arrow 299 shown in FIG. 4). By pivoting the portable imaging device 203 around axis 294, the operator of the ultrasound imaging system 202 may adjust the portable imaging device 203 to be more easily viewable, in one example (e.g., to reduce light glare against the portable imaging device 203, etc.).

The cradle 206, coupled to the mounting bracket 298 of the arm 297 of the pivot assembly 224, is rotatable (e.g., pivotable) in a plurality of directions via the first pivot 223 and second pivot 225. For example, the cradle 206 may pivot toward the ground surface 260 (e.g., in the direction of arrow 299) or away from the ground surface 260 (e.g., in the direction opposite to arrow 299) via the second pivot 225 (e.g., by pivoting the mounting bracket 298 relative to the arm 297 via the second pivot 225, with the mounting bracket 298 fixedly coupled to the cradle 206 such that the mounting bracket 298 and cradle 206 pivot together via the second pivot 225). Additionally, the cradle 206 may pivot around the support stand 204 and parallel to the ground surface 260 (e.g., in the direction of arrow 288, or the direction opposite to arrow 288 as shown in FIG. 4) via the first pivot 223 (e.g., by pivoting the arm 297 relative to the support stand 204 via the first pivot 223).

Because the portable imaging device 203 may couple (e.g., lock) to the cradle 206, pivoting the cradle 206 as described above may pivot the portable imaging device 203 and adjust a position of the portable imaging device 203 relative to the support stand 204 and the ground surface 260. The portable imaging device 203 may be secured to the cradle 206 by inserting the portable imaging device 203 into the cradle 206, as shown in FIGS. 2-4, and, for example, engaging a locking mechanism (not shown) that includes a plurality of hooks coupled to the cradle 206 and a plurality of slots of the portable imaging device 203. The locking mechanism may be released to decouple the portable imaging device 203 from the cradle 206. By configuring the portable imaging device 203 to lock and/or unlock with the cradle 206 via the locking mechanism, the portable imaging device 203 may be easily and quickly coupled and/or decoupled from the cradle 206 (e.g., for transporting the portable imaging device 203 to a different location than other components of the ultrasound imaging system 202, such as the support stand 204, tray 208, etc.).

In some examples, the cradle 206 may be adapted with a lever 1300, shown in FIGS. 13-16, for releasing the portable imaging device 203 from the locking mechanism of the cradle 206. For example, when the portable imaging device 203 is nested in the cradle 206, the locking mechanism may automatically be adjusted to a locked position that maintains the portable imaging device 203 securely within the cradle 206. By applying pressure to the lever, the locking mechanism may be adjusted to an unlocked, disengaged position, allowing the portable imaging device 203 to be removed from the cradle 206 without resistance.

The portable imaging device 203 includes the touch-sensitive display 289, as shown in FIGS. 2 and 4. An operator of the portable imaging device 203 may interact with the touch-sensitive display 289 (e.g., touch the touch-sensitive display with a finger, stylus, etc.) in order to manipulate images shown by the touch-sensitive display 289 and/or navigate a graphical user interface displayed by the touch-sensitive display 289. The touch-sensitive display 289 may also be referred to herein as a touchscreen.

As shown in FIG. 3, the portable imaging device 203 may also include a battery 207 disposed within a housing 205 of the portable imaging device 203, the battery 207 electrically coupled to the controller and a plurality of electronic input connections 215 arranged at a rear surface 211 of the portable imaging device 203. The battery 207 may provide electrical power to the portable imaging device 203 during conditions in which the portable imaging device 203 is decoupled from the cradle 206, for example (e.g., moved to a different location than the support stand 204). However, the battery 207 may also provide electrical power to the portable imaging device 203 (e.g., to the controller and electronic input connections) during conditions in which the portable imaging device 203 is coupled to the cradle 206 (e.g., conditions in which the portable imaging device 203 is seated against the cradle 206 and is not coupled to an external power source, such as an electrical outlet of a wall). The portable imaging device 203 may additionally include other electronic connections adapted to couple the controller to other devices (e.g., electronic storage devices, such as thumb drives having non-transitory computer memory) and/or external power sources.

The ultrasound imaging system 202 may also include a printer assembly 230 and the AC/DC converter case 240 (hereafter, case 240) coupled to the support stand 204, both components positioned below the tray 208 as shown in FIGS. 2-4. In some examples, a bottom surface of the tray 208 may include a securing device for the printer assembly 230, such as a bracket 231 configured to receive a printer 233 and maintain a position of the printer 233. In this way, when the height of the support stand is adjusted, the height of the printer assembly 230 may be similarly adjusted due to coupling of the printer assembly 230 to the sliding arm 270 through the tray 208. The printer 233 may be arranged at a front side 261, as indicated in FIG. 4, of the ultrasound imaging system 202, e.g., in front of the support stand 204 and immediately below the tray 208. The printer 233 may be electronically coupled to the portable imaging device 203 by a cable or through a wireless network communication and configured to receive image data from the portable imaging device 203. The image data may be translated to an image output by the printer 233. The printer assembly 230 may include a loading tray 232 for storing printing media, such as paper, and an output slot 234, as shown in FIG. 2, through which the printing media may emerge during printing.

The case 240 may be a hollow shell formed from a thin but rigid and durable material, such as plastic, adapted to enclose an electronic power device, such as the AC/DC converter. The case 240 may be arranged at a rear side 262, as indicated in FIG. 4, of the ultrasound imaging system 202, opposite of the printer assembly 230. The case 240 may have an outer geometry resembling a cross, with a first portion 302 having a rectangular outer geometry, when viewed in the x-y plane along the z-axis, e.g., as depicted in FIG. 3. The first portion 302 may extend along the axis 201 and have a width 304, defined along the x-axis, similar to a width of the support stand 204. A length 306 of the first portion 302 of the case 240, as shown in FIGS. 3 and 4, is shorter than the length 214 of the support stand 204.

The case 240 has a second portion 308, arranged perpendicular to the first portion 302, extending outwards from side walls 310 of the first portion 302, e.g., away from the axis 201 along the x-axis. The second portion 308 comprises arms 312 that couple to the side walls 310 of the first portion 302 and wrap around the support stand 204 to continue along the z-axis, across side surfaces 314 of the support stand 204. A height 303 of the arms, defined along the y-axis and indicated in FIG. 3, is shorter than the length 306 of the first portion 302 of the case 240.

Figure 6:
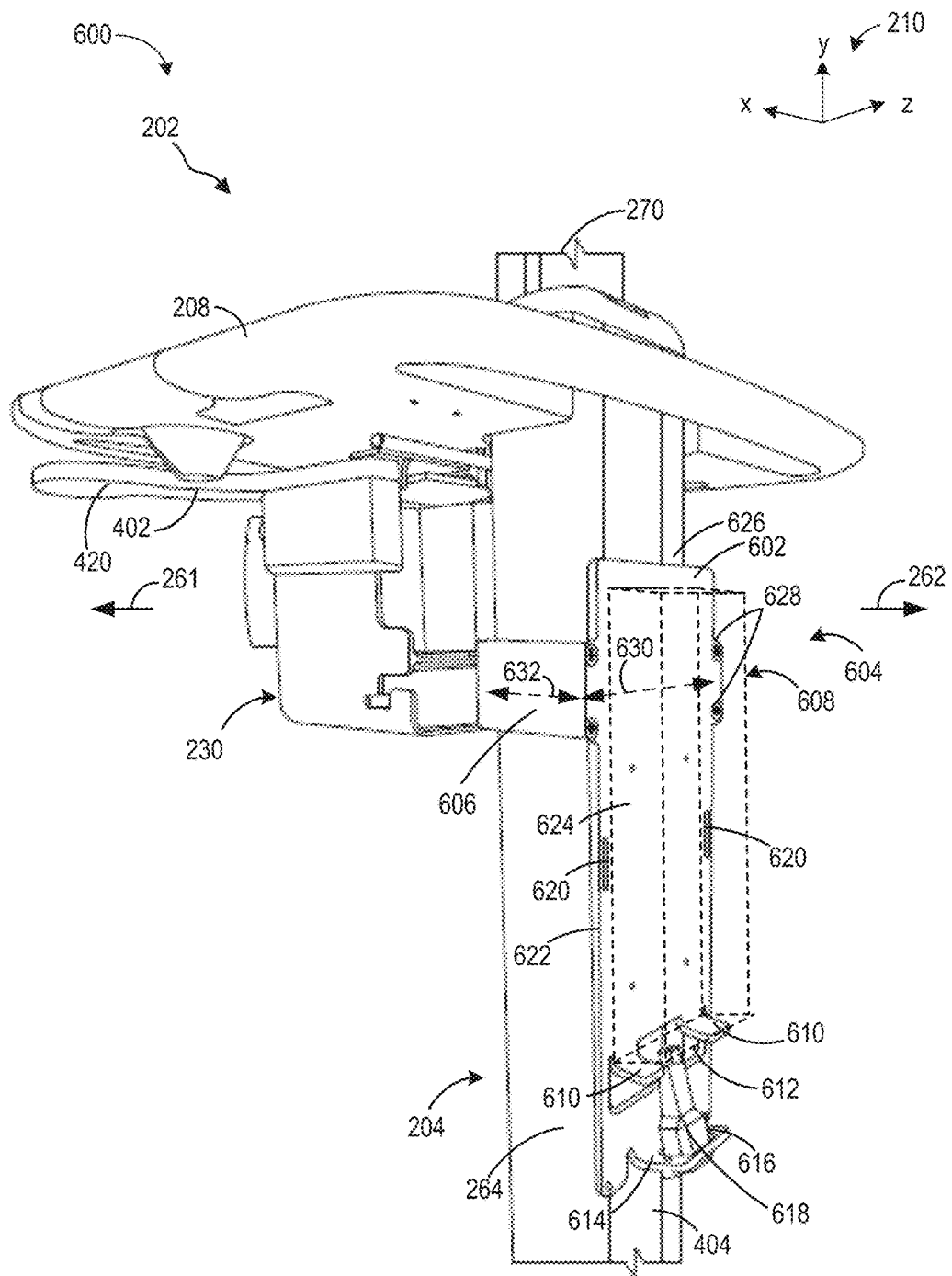
FIG. 6 shows a second perspective of a mounting assembly for the AC/DC converter.

When viewed in the z-y plane, along the x-axis, as depicted in FIG. 4, the case 240 may be coupled to a mounting plate 602, as shown in FIG. 6, that is planar and co-planar with the x-y plane, forming an inner wall of the case 240. As shown in FIG. 4, the mounting plate 602 is proximate to but spaced away from a rear-facing surface 404 of the support stand 204. Details of the mounting plate 602 are described further below with reference to FIG. 6. The case 240 also has an outer wall 405 arranged co-planar with the mounting plate 602 but shorter in length 406 than the mounting plate 602 (e.g., shorter than the overall length 306 of the case 240).

The outer wall 405 of the case 240 may be coupled to the mounting plate 602 by the side walls 310 of the case 240 as well as by a curved upper wall 408 and a curved lower wall 410. The upper wall 408 and the lower wall 410 may be similarly shaped but curve in opposite directions, away from one another. The lower wall 410 may include a port to allow a power cable 412, as shown in FIGS. 2-4, to be inserted through the port to couple to the AC/DC converter at a first end 414 of the power cable 412. Furthermore, the port may be shaped to accept a bifurcated cable. As shown, the case 240 covers lateral sides of a power pack. However, other case contours have been envisioned.

FIG. 10 shows another view of the ultrasound imaging system 202 with a power pack 1000. The power pack 1000 is designed to for example, convert AC current to DC current. As such, the power pack 1000 may include an AC/DC converter. The power pack 1000 may receive electrical power via a bifurcated power cable 1002. The bifurcated power cable 1002 specifically includes a first cable 1004 attached to the power pack 1000 and a second cable 1006 attached to the printer assembly 230, shown in FIG. 5. In this way, the bifurcated cable can provide electrical power to multiple components in the system. The bifurcated cable 1002 also includes an interface 1006. The interface 1006 is designed to attach to a power cable which may be attached to a power source, such as a wall outlet. A cable bracket 1008 supports the interface 1006. FIG. 10 also shows attachment apparatuses 1010 (e.g., screws) which may be used to mount the case 240, shown in FIGS. 2-4, to the mounting plate 602. Additionally, the power pack 1000 is supported by the braces 610 of the mounting plate 602. Specifically, in the illustrated embodiment two braces 610 are provided in the system. Providing two braces facilitates desired cable alignment. However, mounting plates with alternate numbers of braces may be used, in other embodiments. The mounting plate 602 also allows the power pack 1000 to be mounted on a side of the column 264 opposing the ultrasound assembly to counterbalance the weight of the ultrasound assembly (e.g., display, tray, printer, etc.) In this way, the system may be weighted to increase system stability. As a result, the likelihood of the system tipping over is reduced. Furthermore, the mounting plate 602 and power pack 1000 maintain a set distance from the ultrasound assembly.

FIG. 10 also shows the arms 312 attached (e.g., removably attached) to the mounting plate 602. It will be appreciated that the power pack 1000 may be moved up and down the column 264 as the height of the tray 208, shown in FIGS. 2-4, is adjusted. Additionally, a strap 1012 is also shown extending around the power pack 1000 to secure the pack to the mounting plate 602. The strap 1012 may be constructed out of hook and loop fabric. The strap 1012 may additionally or alternatively includes hooks, clips, etc., for securing the strap around the power pack 1000. In other embodiments however, the strap may be omitted from the system.

The case 240 may include an upper cable hook 316 coupled to and extending upwards, along the y-axis, from the outer wall 405 as well as a lower cable tab 318, coupled to and extending downwards from the outer wall 405. The upper cable hook 316 and the lower cable tab 318 form a cable management system to organize and maintain a position of the power cable 412 so that the power cable 412 does not impede movement of the ultrasound imaging system 202 along the ground surface 260.

For example, in FIGS. 2-4, the power cable 412 is shown inserted through the port in the lower wall 410 of the case 240 at the first end 414 of the power cable 412 but unattached at a second end 416, where a power plug 418 is disposed. The power cable 412 may be looped around the upper cable hook 316 multiple times to allow the power cable 412 to be readily accessed and unwound from the upper cable hook 316 while maintaining the power cable 412 off the ground surface 260. Alternatively, it may be desirable to loop the cable around both the upper cable hook 316 and the lower cable tab 318, e.g., circling around and extending between the upper cable hook 316 and the lower cable tab 318, particularly if the power cable 412 is longer than shown in FIGS. 2-4.

The power plug 418 is adapted to couple to a power outlet (not shown) to supply electrical power to the ultrasound imaging system 202. As such, the AC/DC converter housed within the case 240 may be an intermediary between the power outlet and the ultrasound imaging system 202, converting AC flow from the power outlet to DC flow before the current is delivered to the electronically actuated components of the ultrasound imaging system 202, such as the portable imaging device 203 and probes coupled to the portable imaging device 203. By coupling the AC/DC to the support stand 204 via the case 240, a distance between the AC/DC converter and the portable imaging device 203 is fixed as a result of coupling of both components to the sliding arm 270 of the support stand 204.

FIG. 17 shows another view of the ultrasound imaging system 202. The AC/DC converter is again shown housed within the case 240. A power cable 1700 is shown extending through the case 240 and is coupled to the AC/DC converter. The power cable 1700 is shown extending from a bottom side 1702 of the case 240. An upper cable hook 316 is shown extending from a top side 1704 of the case 240. The cable hook 316 allows the cable 1700 be wrapped around when it is unplugged. The cable hook 316 may be flexible, in one example. Designing the hook with flexion allows the cable to release from the hook if for example the cart is pulled away from a power outlet while charging and a portion of the cable has been left on the hook. In this way, the likelihood of the cable interfering with movement of the system is reduced. However, in other examples, the hook may be less flexible or omitted from the system. FIG. 17 also shows the column 264, arms 312, and tray 208.

A positioning of the case 240 relative to the tray 208, the printer assembly 230, and the support stand 204 is shown in a first perspective view 500 in FIG. 5. The case 240 is arranged below the tray 208, with respect to the y-axis. The arms 312 of the second portion 308 of the case 240 are aligned, along the z-direction, with the loading tray 232 of the printer assembly 230. However, in other examples the case 240 may be positioned so that the arms 312 of the case 240 are higher or lower than the loading tray 232, with respect to the y-axis. The case 240 may be spaced away from the tray 208 so that there is clearance between the case 240 and the tray 208 to allow winding of a power cable, e.g., the power cable 412 of FIGS. 2-4, around the upper cable hook 316.

The first perspective view 500 of FIG. 5 shows that the arms 312 of the second portion 308 of the case 240 have a curved surface, curving around the support stand 204 as the arms 312 extend away from the first portion 302 of the case 240 along the x-axis and continue along the z-axis, curving through a perpendicular angle as the arms 312 transition from the x-axis to the z-axis. The arms 312 may terminate at ends 502 of the arms 312, the ends 502 having edges aligned with the y-axis. The arms 312, adapted as hollowed extensions from the case 240, may have inner edges that are proximate to the column 264 of the support stand 204 and extend across surfaces of the column 264 but are spaced away from the column 264 so that the arms 312 do not contact the column 264. By maintaining a space between the arms 312 and surfaces of the column 264, when the sliding arm 270 of the support stand 204 is adjusted up and down, the case 240 may also slide up and down along the support stand 204, uninhibited by contact between the case 240 and the stationary column 264 of the support stand 204.

The lever 402 is also shown in FIG. 5 as a curved, elongate element extending along the x-z plane. The lever 402 may be adjustable between a first, locked position and a second, unlocked position. For example, an orientation of the lever shown in FIG. 5 may be the locked position where the sliding arm 270 of the support stand 204 is locked at a height shown. By applying pressure to an outer end 420 of the lever 402, in a direction indicated by arrow 422, the sliding arm 270 may be unlocked and slid up or down along the y-axis axis by pulling or pushing on the tray 208, relative to the column 264 of the support stand 204. Alternatively, the lever 402 may be configured may be unlocked by applying pressure and pivoting the lever 402 in a direction opposite of arrow 422.

When the lever 402 is in the unlocked position and the sliding arm 270 is able to slide up or down along the front channel 272 of the support stand 204, movement of the sliding arm 270 is translated to the case 240 by a power pack mounting assembly 604, as shown in a second perspective view 600 in FIG. 6. The second perspective view 600 shows the ultrasound imaging system 202 with the case 240 removed from the power pack mounting assembly 604. The power pack mounting assembly 604 includes the mounting plate 602, a power pack mounting bracket 606, and an AC/DC converter 608, depicted with a dashed outline.

The mounting plate 602, as described above, may be coplanar with the rear-facing surface 404 of the support stand 204 and spaced away from the support stand 204. The mounting plate 602 may include a pair of braces 610, configured to be in contact with and support a bottom end 612 of the AC/DC converter 608 to maintain a position of the AC/DC converter 608 within the case 240. The mounting plate 602 also has a bottom brace 614 that includes an opening 616 through which a power plug 618 may be inserted. The power plug 618 may be attached to the first end 414 of the power cable 412 shown in FIGS. 2-4, adapted to couple to the AC/DC converter 608 to flow current to the AC/CD converter 608 from an electrical outlet. The power plug 618 may be plugged into a socket at the bottom end 612 of the AC/DC converter 608, the socket positioned between the pair of braces 610 of the mounting plate 602.

The mounting plate 602 also includes slots 620, the slots 620 extending entirely through a thickness, as defined along the z-axis, of the mounting plate 602 and aligned with the y-axis. The slots 620 may be disposed proximate to side edges 622 of the mounting plate 602, aligned with sides 624 of the mounting plate 602. A strap, such as a Velcro strap, may be threaded through the slots 620 and used to secure the AC/DC converter 608 to the mounting plate 602. The case 240 may be configured to accommodate the strap and fit over the mounting plate 602 and strap. For example, the case 240 may have a lip at an upper edge of the case 240 that may hook over a top edge 626 of the mounting plate 602. In other examples, the case 240 may snap into place over the mounting plate 602 or be secured to the mounting plate 602 by a type of fastening mechanism.

The mounting plate 602 may be secured to the power pack mounting bracket 606 by a plurality of screws 628. As one example, the power pack mounting bracket 606 may have a rectangular geometry with curved corners (when viewed along the y-axis), wrapping around the column 264 of the support stand 204. Dimensions of the power pack mounting bracket 606, e.g., a width 630 and a depth 632, may be larger than a width and a depth of the column 264 so that inner surfaces of the power pack mounting bracket 606 do not contact surfaces of the support stand 204, e.g., the power pack mounting bracket 606 is spaced away from all outer surfaces of the column 264. In other examples, the power pack mounting bracket 606 may be C-shaped with an opening of the C aligned with the mounting plate 602, each end of the C coupled to two vertically aligned screws of the plurality of screws 628 at the mounting plate 602.

Figure 7:
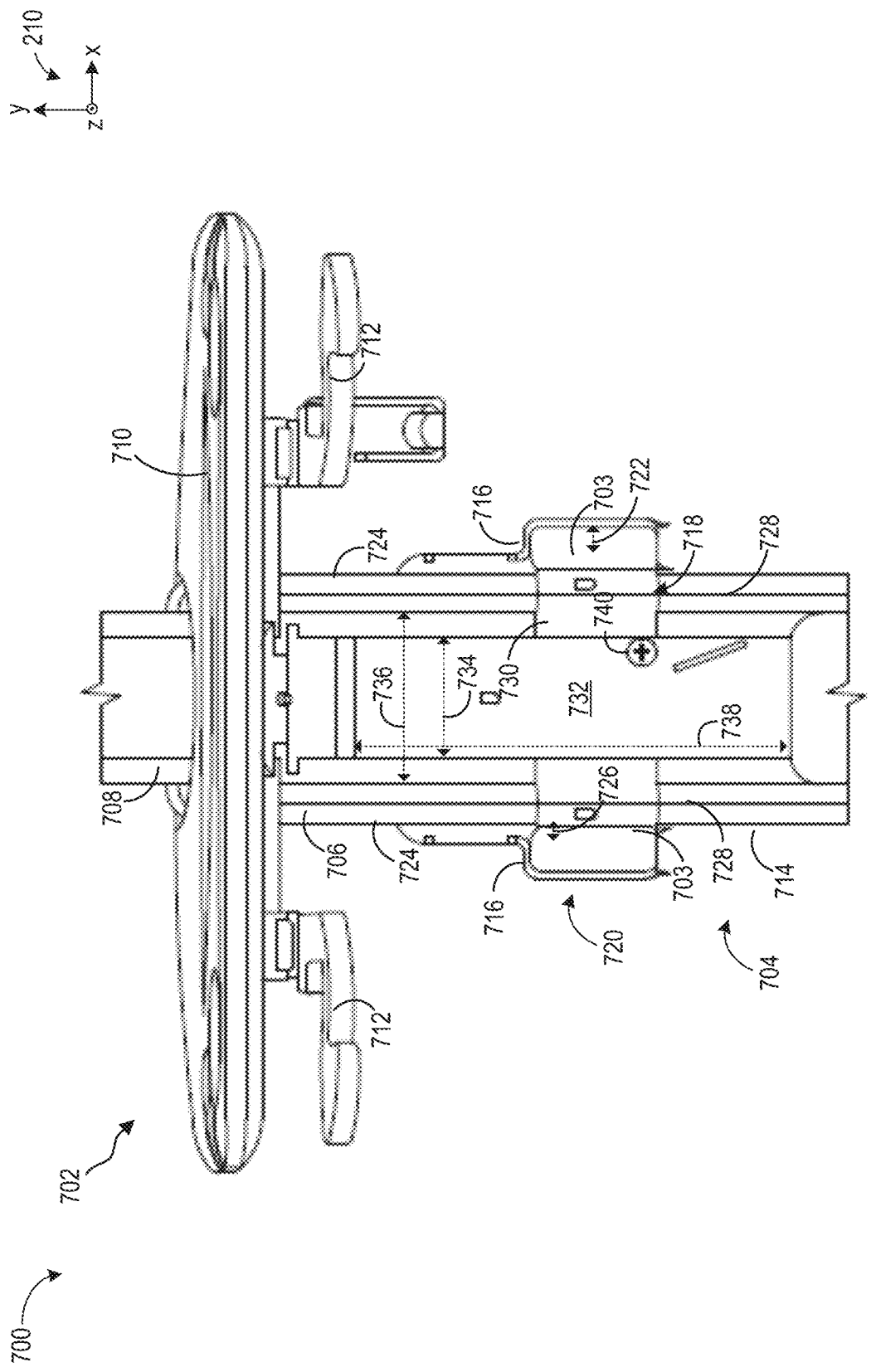
FIG. 7 shows a front view of a second embodiment of an ultrasound imaging system.
Figure 8:
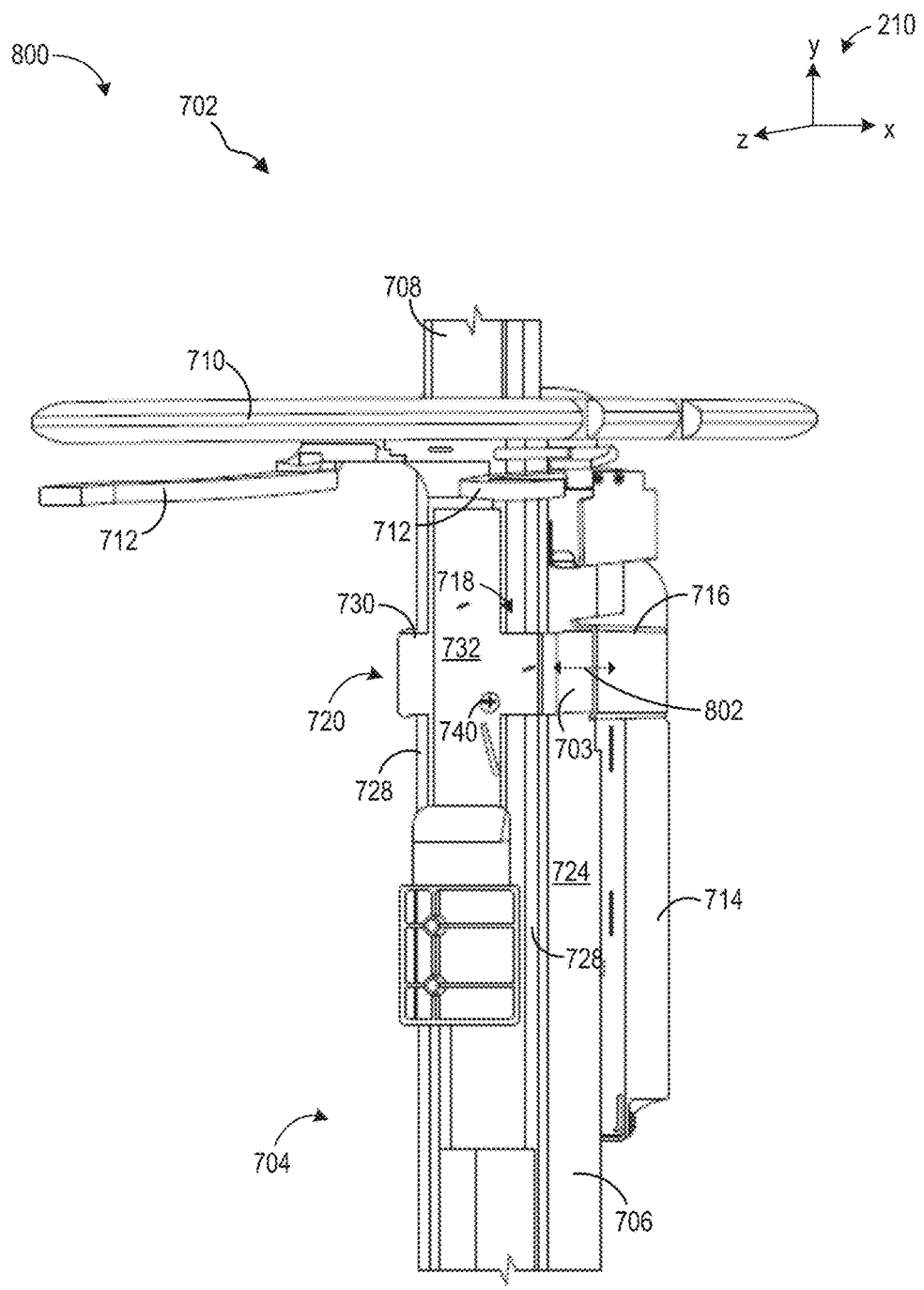
FIG. 8 shows a perspective view of the ultrasound imaging system.

A second embodiment of an ultrasound imaging assembly 702 is shown from a front view 700 in FIG. 7 and a perspective view 800 in FIG. 8. The ultrasound imaging assembly 702 may be similarly configured as the ultrasound imaging system 202 of FIGS. 2-6, having common components that are numbered differently in FIGS. 7-8 but will not be re-introduced for brevity. The ultrasound imaging assembly 702 is shown with a support stand 704, the support stand 704 including a stationary column 706 and a sliding arm 708. A tray 710 is coupled to the sliding arm 708 and includes a pair of levers 712 for lock/unlocking a position of the sliding arm 708 relative to the column 706, rather than a single lever as shown in FIGS. 4 and 5.

The ultrasound imaging assembly 702 is shown in FIGS. 7-8 without a printer assembly, e.g., the printer assembly 230 of FIGS. 2-6, for clarity of view. In some examples, the printer assembly may instead be an electrocardiogram (ECG) assembly with an ECG machine coupled to the support stand 704 by a bracket. While neither the printer assembly or the ECG assembly are shown in FIGS. 7-8, the printer or ECG assembly may be positioned at a front side of the ultrasound imaging assembly 702, under the tray 710.

A case 714 for housing an AC/DC converter is coupled at a rear-facing side of the support stand 704. Arms 716 of the case 714 extend around sides of the support stand, each arm positioned over and surrounding opposite sides 703, e.g., arranged on opposite sides of the support stand 704, of a power pack mounting bracket 718 of a power pack mounting assembly 720. As shown in FIG. 7, the arms 716 of the case 714 are spaced away from the sides 703 of the power pack mounting bracket 718 by a first distance 722 and the sides 703 of the power pack mounting bracket 718 may be spaced away from side surfaces 724 of the column 706 of the support stand 704 by a second distance 726. As shown in FIG. 8, the arms 716 of the case 714 may extend along at least a portion of a depth 802 of the sides 703 of the power pack mounting bracket 718, parallel with the z-axis.

The power pack mounting bracket 718 may curve around front edges 728 of the column 706, as shown in FIGS. 7 and 8, spaced away from the front edges 728, and couple to the sliding arm 708 of the support stand 704 at a front face 730 of the power pack mounting bracket 718. The power pack mounting bracket 718 may be secured to the sliding arm 708 by a locking plate 732. The locking plate 732 may be rectangular, with a width 734 narrower than a width 736 of the sliding arm 708, defined along the x-axis, and a length 738 shorter than a length of the sliding arm 708, as shown in FIG. 7. Both the locking plate 732 and the front face 730 of the power pack mounting bracket 718 may have an aperture that, when aligned, allows a screw 740 to be threaded therethrough, attaching the power pack mounting bracket 718 and locking plate 732 to the sliding arm 708. The power pack mounting bracket 718 may thus be readily removed by unthreading the screw 740 to release the locking plate 732 and the power pack mounting bracket 718.

The portable ultrasound imaging system, a height of an ultrasound imaging assembly may be varied, simultaneously adjusting heights of components such as a support stand, a portable imaging system, a tray, a cradle, and an AC/DC converter, all in unison. The components may each be coupled to a sliding arm of the support stand, the sliding arm adapted to be vertically mobile relative to a stationary column of the support stand. The AC/DC converter may be housed within a case that is positioned at a rear side of the support stand and secured to the sliding arm by a mounting assembly, including a mounting plate and a mounting bracket. A simplified, integrated adjustment of the components of the ultrasound imaging assembly is achieved while maintaining a balanced weight distribution of the components by positioning the AC/DC converter at the rear side of the support stand, countering a weight of the tray and the portable imaging system, both biased towards a front side of the ultrasound imaging assembly. Furthermore, the AC/DC converter case may provide a shield between external objects and the AC/DC converter while a cable management system of the case may maintain a position of system cables off a ground surface, reducing a likelihood of entanglement and maintaining the AC/DC converter at a fixed distance relative to the portable imaging system and the cradle. A simplicity and efficiency of height adjustment is increased, thereby reducing an amount of time expended on positioning the ultrasound imaging assembly into a comfortable configuration and thus enhancing an operational workflow.

Figure 11B:
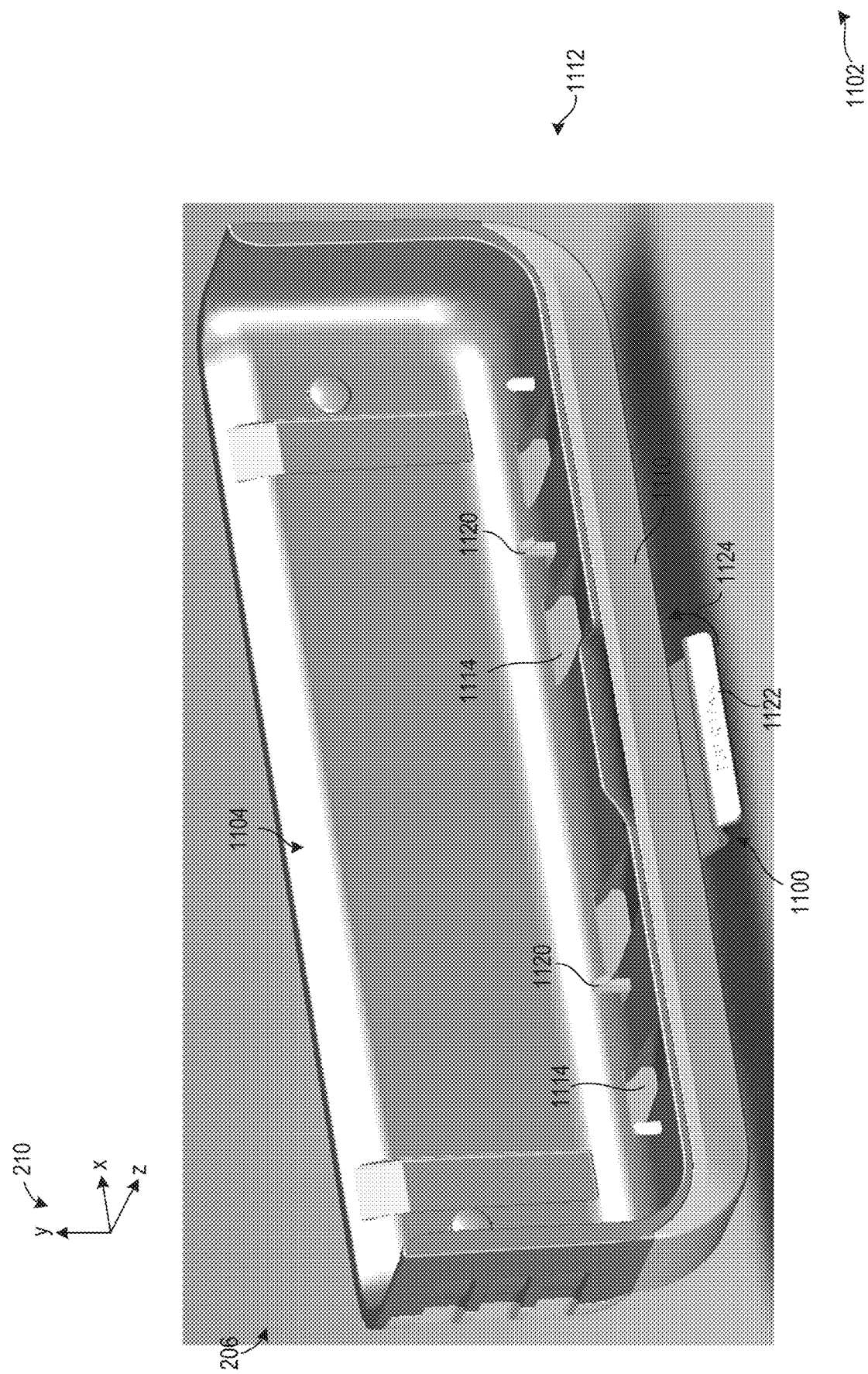
FIG. 11B shows a detailed front view of the cradle included in the ultrasound imaging system.
Figure 12:
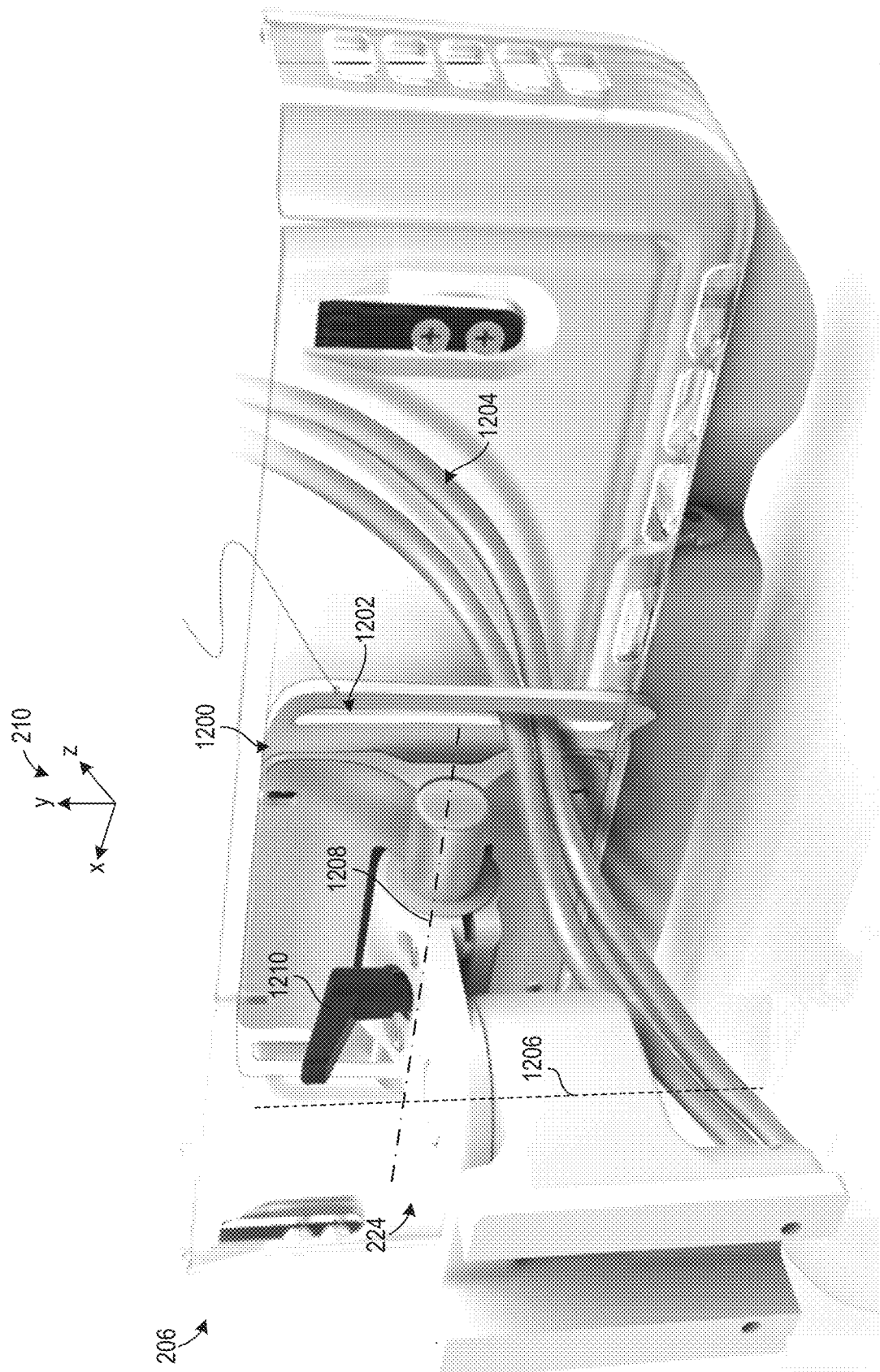
FIG. 12 shows another view of the cradle and pivoting assembly included in the ultrasound imaging system.

FIG. 11A shows a detailed view of a backside of the cradle 206 and FIG. 11B shows a detailed view of a frontside of the cradle 206. The cradle 206 is designed to support an imaging device, such as the portable imaging device 203 of FIGS. 2-4. As such, the cradle 206 includes an opening 1104 configured to receive the imaging device, as shown in FIG. 11B. The cradle 206 also includes brackets 1100, as shown in FIG. 11A, allowing the cradle 206 to be attached to the sliding portion of the support stand. A mounting interface 1102 is configured to attach to the pivoting interface of the support stand, also shown in FIG. 11A.

The cradle 206 has a release lever 1106, extending through a slot 1108 disposed in a bottom surface 1110 of the cradle 206. A lower region 1112 of the cradle 206, with respect to the y-axis, may include a plurality of openings 1114 to accommodate various cables coupling to ports in the display device. The release lever 1106 may extend outwards, away from the bottom surface 1110, and have a geometry including curved portions and planar portions, coupled together by edges. A width 1116 of the release lever 1106 is narrower than a width 1118 of the cradle 206, the widths defined along the x-axis, as shown in FIG. 11A.

The release lever 1106 may be a component of a release mechanism of the cradle 206 that also includes hooks 1120, as shown in FIG. 11B. The hooks 1120 may engage with detents in the display device to secure the display device to the cradle 206 when the release lever 1106 is in a neutral position, e.g., a position shown in FIGS. 11A and 11B. When the release lever 1106 is actuated by pulling a free end 1122 of the release lever 1106 upwards, as indicated by arrow 1124, the hooks 1120 may be disengaged from the detents of the display device to allow the display device to be removed from the cradle 206. Details of the release mechanism are described further below with reference to FIGS. 13-16.

FIG. 12 shows a detailed view of the cradle 206 and the pivot assembly 224. The pivot assembly 224 is designed to allow the cradle 206 to pivot about a vertical axis 1206 and a horizontal axis 1208, in the depicted embodiment. For example, the cradle 206 may freely pivot around the vertical axis 1206 along the x-z plane, as adjusted by an operator. The cradle 206 may also pivot about the horizontal axis 1208, along the y-z plane to be tilted to a desired angle by the operator. The pivot assembly 224 may include a locking handle 1210 to lock a position of the cradle 206 when the cradle is tilted to the desired angle. As an example, the locking handle 1210 is shown in a locked position in FIG. 12, inhibiting further tilting of the cradle about the horizontal axis 1208. When the locking handle 1210 is pulled upwards, along the y-axis, the locking handle 1210 is adjusted to an unlocked position, allowing the cradle 206 to be pivoted about the horizontal axis 1208. Alternatively, the locking handle 1210 may be unlocked by pushing down on the locking handle 1210 and locked by pulling upwards.

In other examples, the pivot assembly 224 may allow the cradle to articulate along additional or alternate paths, besides the horizontal and vertical axes shown in FIG. 12. For example, the pivot assembly 224 may include a ball joint allowing the cradle 206 to be pivoted through a wide range of angles through a vertical, horizontal and transverse axis at a single joint. In this way, the cradle may be tilted to diagonal angles relative to the axes.

A mounting plate 1200 is shown in FIG. 12 including cable slots 1202. The slots 1202 allow cables 1204 to be efficiently routed therethrough. For instance, wires such as USB cords, power cords, etc., may be routed through the slots. In this way, cables may be efficiently routed in the system. In this way, the cables may hang and stay near the imaging device once unplugged from the device, thereby reducing the chance of unwanted cable pinching, snagging, etc.

Figure 13:
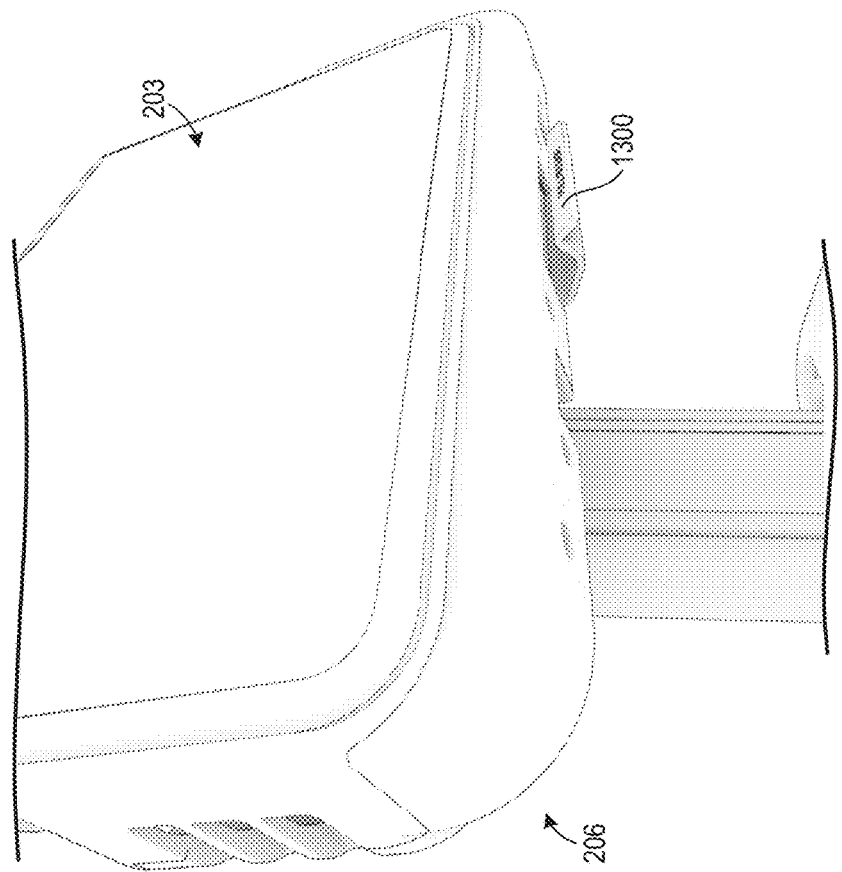

FIG. 13 shows a detailed view of the cradle 206 and the portable imaging device 203. The cradle 206 includes a release lever 1300, which may be used similarly as the release lever 1106 shown in FIGS. 11A-11B, designed to release the device 203 from the cradle 206 when actuated. The release lever 1300 may be attached to mechanical components such as hooks which when actuated are released from the portable imaging device 203.

Figure 14A:
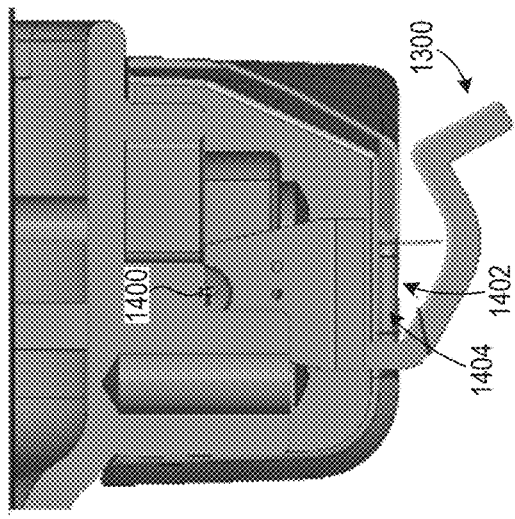
FIGS. 13-16 show different views of a release lever and associated mechanical components included in the cradle for releasing the portable imaging device from the cradle.
Figure 14B:
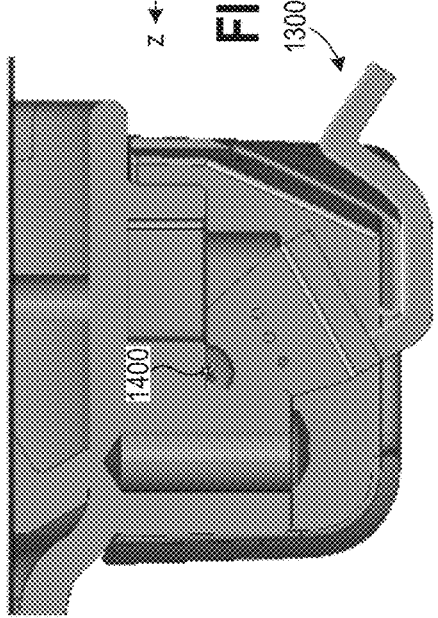
Figure 15:
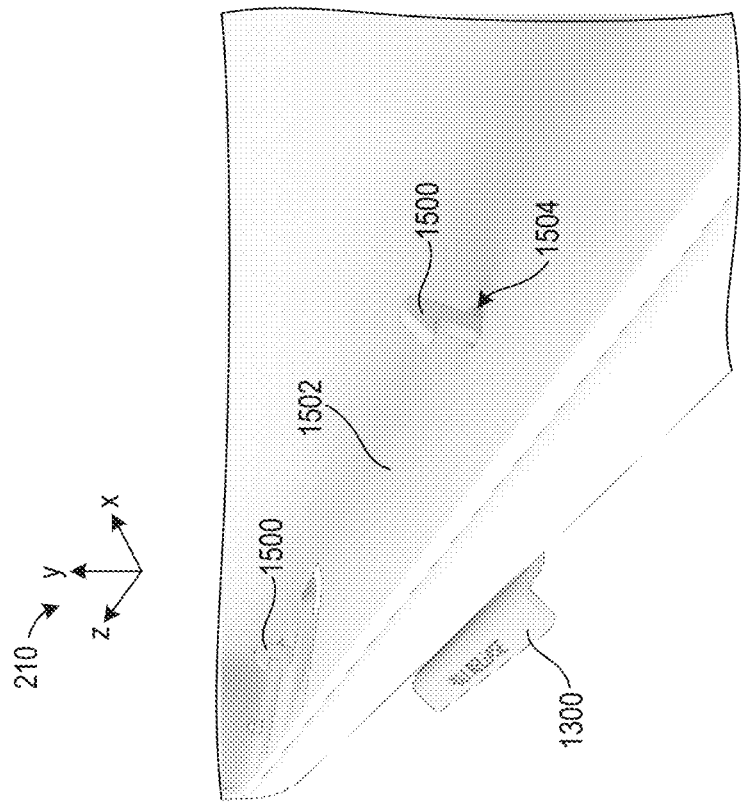

FIGS. 14A and 14B show a side view of the release lever 1300. Specifically, FIG. 14A shows the lever 1300 in a closed position and FIG. 14B shows the lever 1300 in an open position subsequent to lever actuation by a user. The lever 1300 is shown pivoting about axis 1400. In the closed position shown in FIG. 14A hooks 1500, shown in FIG. 15, are engaged with detents in the portable imaging device 203. The hooks 1500 are shown extending through a bottom wall 1502 of the cradle 206. The bottom wall 1502 include openings 1504 accommodating movement of the hooks 1500. However, alternate hook positions have been contemplated. FIG. 16 shows one of the hooks 1500 engaged with a detent 1600 in the portable imaging device 203. Conversely, in the open position shown in FIG. 14B the hooks 1500, shown in FIG. 15, are disengaged from detents in the portable imaging device 203. FIG. 14A also shows a cover recess 1402. The cover recess 1402 facilitates lever actuation. It will be appreciated that a user may quickly and efficiently actuate the lever to detach the portable imaging device from the cradle. As a result, the operational efficiency of the ultrasound imaging system may be further increased.

The technical effect of coupling the components of the ultrasound imaging assembly to a vertically mobile portion of the support stand, and in particular, the AC/DC converter, is to enable height adjustment of the components in an efficient, simultaneous manner.

FIGS. 1-17 show example configurations with relative positioning of the various components. If shown directly contacting each other, or directly coupled, then such elements may be referred to as directly contacting or directly coupled, respectively, at least in one example. Similarly, elements shown contiguous or adjacent to one another may be contiguous or adjacent to each other, respectively, at least in one example. As an example, components laying in face-sharing contact with each other may be referred to as in face-sharing contact. As another example, elements positioned apart from each other with only a space therebetween and no other components may be referred to as such, in at least one example. As yet another example, elements shown above/below one another, at opposite sides to one another, or to the left/right of one another may be referred to as such, relative to one another. Further, as shown in the figures, a topmost element or point of element may be referred to as a "top" of the component and a bottommost element or point of the element may be referred to as a "bottom" of the component, in at least one example. As used herein, top/bottom, upper/lower, above/below, may be relative to a vertical axis of the figures and used to describe positioning of elements of the figures relative to one another. As such, elements shown above other elements are positioned vertically above the other elements, in one example. As yet another example, shapes of the elements depicted within the figures may be referred to as having those shapes (e.g., such as being circular, straight, planar, curved, rounded, chamfered, angled, or the like). Further, elements shown intersecting one another may be referred to as intersecting elements or intersecting one another, in at least one example. Further still, an element shown within another element or shown outside of another element may be referred as such, in one example.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc., are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A portable ultrasound imaging system, comprising: a support stand with a sliding portion vertically slidable in relation to a stationary portion; a cradle configured to support an ultrasound imaging device, the cradle coupled to the sliding portion of the support stand; a tray, positioned below the cradle, coupled to the sliding portion of the support stand; a case at least partially enclosing an electric power converter electrically coupled to the ultrasound imaging device by an electric power cable, positioned at a rear side of the support stand and removably coupled to the sliding portion of the support stand such that the sliding portion, the cradle, the tray, the case, and the electric power converter move in unison during sliding movement of the sliding portion, and a pair of levers coupled to the sliding portion of the support stand and arranged below the tray; wherein a distance between the electric power converter and each of the cradle and the tray is maintained constant during the sliding movement of the sliding portion; wherein unified adjustment of a position of the cradle, the tray, the case, and the electric power converter, continuously along a height of the support stand, is enabled based on adjustment of the pair of levers between a locked position and an unlocked position; and wherein the case includes a pair of arms wrapping around sides of the support stand perpendicular to the rear side of the support stand, wherein a height of each arm of the pair of arms along a vertical axis is shorter than a length of the case.

2. The portable ultrasound imaging system of claim 1, wherein the pair of levers are configured to lock and unlock the sliding portion to the stationary portion of the support stand.

3. The portable ultrasound imaging system of claim 1, further comprising a mounting assembly coupled to the case and extending between the case and the sliding portion of the support stand.

4. The portable ultrasound imaging system of claim 3, wherein the mounting assembly includes a mounting plate forming an inner wall of the case, the mounting plate in contact with the electrical converter, positioned at a rear surface of the support stand and aligned co-planar with the rear surface.

5. The portable ultrasound imaging system of claim 4, wherein the mounting plate is spaced away from the rear surface of the support stand and a position of the mounting plate is maintained by a mounting bracket.

6. The portable ultrasound imaging system of claim 5, wherein the mounting bracket circumferentially surrounds the support stand and is spaced away from surfaces of the stationary portion of the support stand, coupling to the sliding portion of the support stand at a front side of the support stand.

7. The portable ultrasound imaging system of claim 6, wherein the case has a body, extending vertically and parallel with an axis of the support stand, and a plurality of arms extending horizontally away from the body of the case and along the mounting bracket, and wherein the plurality of arms are removably attached to the mounting plate and wrap around the support stand, along side surfaces of the support stand.

8. The portable ultrasound imaging system of claim 7, wherein the case has a first cable tab extending upwards along the axis of the support stand from an upper region of an outer wall of the case and a second cable tab extending downwards along the axis from a bottom region of the outer wall of the case, the first and second cable tabs configured to engage with a power cable and maintain the power cable above a ground surface.

9. An ultrasound imaging assembly, comprising: a support stand aligned with a vertical axis and configured to adjust a height of an imaging system displaying information obtained from an ultrasound transducer, the imaging system coupled to a vertically mobile portion of the support stand; a cradle positioned at an upper end of the vertically mobile portion of the support stand configured to receive an ultrasound imaging device; a tray positioned below the ultrasound imaging device and coupled to the vertically mobile portion of the support stand; a pair of levers, oriented at a front side of the support stand, configured to engage with the vertically mobile portion of the support stand; and a power pack assembly arranged below the tray and including a case removably coupled to the vertically mobile portion of the support stand by a mounting bracket, wherein the power pack assembly and the case are configured to move in unison with the vertically mobile portion of the support stand; wherein a distance between the power pack assembly and each of the cradle and the tray is maintained constant during movement of the vertically mobile portion of the support stand; wherein the power pack assembly, the case and the vertically mobile portion of the support stand move in unison and are continuously adjustable in height based on adjustment of the pair of levers between a locked position and an unlocked position; and wherein the case includes a pair of arms wrapping around side surfaces of the support stand, wherein a height of each arm of the pair of arms along the vertical axis is shorter than a length of the case.

10. The ultrasound imaging assembly of claim 9, wherein the support stand is adjustable through a plurality of heights between fully extended and fully retracted configurations of the mobile portion and a distance between the power pack assembly and the cradle is maintained constant at any height of the plurality of heights.

11. The ultrasound imaging assembly of claim 9, wherein the pair of levers is a locking mechanism configured to lock the mobile portion to the stationary portion of the support stand when pivoted to a first position and configured to unlock the mobile portion from the stationary portion when pivoted to a second position.

12. The ultrasound imaging assembly of claim 9, wherein the imaging system is coupled to the mobile portion of the support stand by the cradle and a pivotable arm extending between the cradle and the support stand.

13. The ultrasound imaging assembly of claim 12, wherein a positioning of each of the cradle, the pivotable arm, and the imaging system is biased towards a front side of the ultrasound imaging assembly.

14. The ultrasound imaging assembly of claim 13, wherein the power pack assembly includes an outer housing for an electrical converter, the outer housing and electrical converter positioned at a rear side of the ultrasound imaging assembly, below the tray.

15. An ultrasound imaging assembly, comprising: a support stand; a cradle, supporting a display device, coupled to the support stand; a tray positioned below the cradle and coupled to the support stand; a pair of levers arranged below the tray and configured to enable adjustment of a position of the tray vertically along the support stand; and a power pack mounting assembly positioned below the pair of levers and coupled to the support stand, the power pack mounting assembly configured to move vertically with the tray, and including a hollow case coupled to a mounting plate, the hollow case having a pair of aims wrapping around surfaces of the support stand, wherein a height of each arm of the pair of arms along a vertical axis is shorter than a length of the hollow case, and the mounting plate connected to the support stand by a mounting bracket wrapping around the surfaces of the support stand, and cable management elements disposed on an outer surface of the hollow case, and wherein at least a portion of the mounting bracket is spaced away from the surfaces of the support stand; wherein a distance between the power pack mounting assembly and each of the cradle and the tray is maintained constant during vertical movement of the power pack mounting assembly; and wherein unified movement of the power pack mounting assembly, the cradle, and the tray through continuous height adjustments is enabled by adjustment of the pair of levers between a locked position and an unlocked position.

16. The ultrasound imaging assembly of claim 15, wherein the hollow case is configured to enclose an electrical converter and be removably coupled to the mounting plate.

* * * * *